US012648839B2

(12) United States Patent
  Irwin et al.

(10) Patent No.: US 12,648,839 B2
(45) Date of Patent: Jun. 9, 2026

(54) WEARABLE PERINEUM LEAKAGE CONTROL DEVICE

(71) Applicant: Her Secure, Inc., Plantation, FL (US)

(72) Inventors: Nicholas Irwin, Plantation, FL (US);
    Mark Polyak, Hollywood, FL (US)

( * ) Notice: Subject to any disclaimer, the term of this
    patent is extended or adjusted under 35
    U.S.C. 154(b) by 50 days.

(21) Appl. No.: 18/555,518

(22) PCT Filed: Apr. 27, 2022

(86) PCT No.: PCT/US2022/026493
    § 371 (c)(1),
    (2) Date: Oct. 14, 2023

(87) PCT Pub. No.: WO2022/232238
    PCT Pub. Date: Nov. 3, 2022

(65) Prior Publication Data

US 2024/0189086 A1     Jun. 13, 2024

Related U.S. Application Data

(60) Provisional application No. 63/182,335, filed on Apr.
    30, 2021.

(51) Int. Cl.
    *A61F 2/00*      (2006.01)
    *A61F 13/15*     (2006.01)
    *A61F 13/472*    (2006.01)
    *A61F 13/56*     (2006.01)
(52) U.S. Cl.
    CPC ...... *A61F 2/0009* (2013.01); *A61F 13/47209*
        (2013.01); *A61F 13/5605* (2013.01); *A61F*

*2013/15121* (2013.01); *A61F 2250/0007*
(2013.01); *A61F 2250/0012* (2013.01)

(58) Field of Classification Search
    CPC ...... A61F 5/24; A61F 5/28; A61F 5/32; A61F
        2/0009; A61F 13/47209; A61F 13/5605;
        A61F 2013/15121; A61F 2250/0007;
        A61F 2250/0012; A61F 13/202; A61H
        2011/005; A61H 2205/085; A61H 11/00;
        A61H 7/001; A61H 2201/1652; A61B
        17/00; A61B 17/0057
    See application file for complete search history.

(56) References Cited

FOREIGN PATENT DOCUMENTS

CN        209611450 U  * 11/2019

* cited by examiner

*Primary Examiner* — Ophelia A Hawthorne
(74) *Attorney, Agent, or Firm* — Skaar Ulbrich Macari,
P.A.

(57) ABSTRACT

A perineum control device configured to apply pressure to
the perineum of a wearer for the purpose of controlling
various conditions including leakages of body fluids from
the urethral, anal, and vaginal openings. The device includes
one or more front and rear retractors having a retractable
cord supporting a bridge or band member that is positioned
against a wearer's perineum in order to exert a constant and
predetermined upward compression force, thereby increas-
ing the perineum pressure above an abdominal or bladder
pressure preventing or mitigating leakages and/or prolapses.

20 Claims, 22 Drawing Sheets

POSTERIOR VIEW

ANTERIOR VIEW

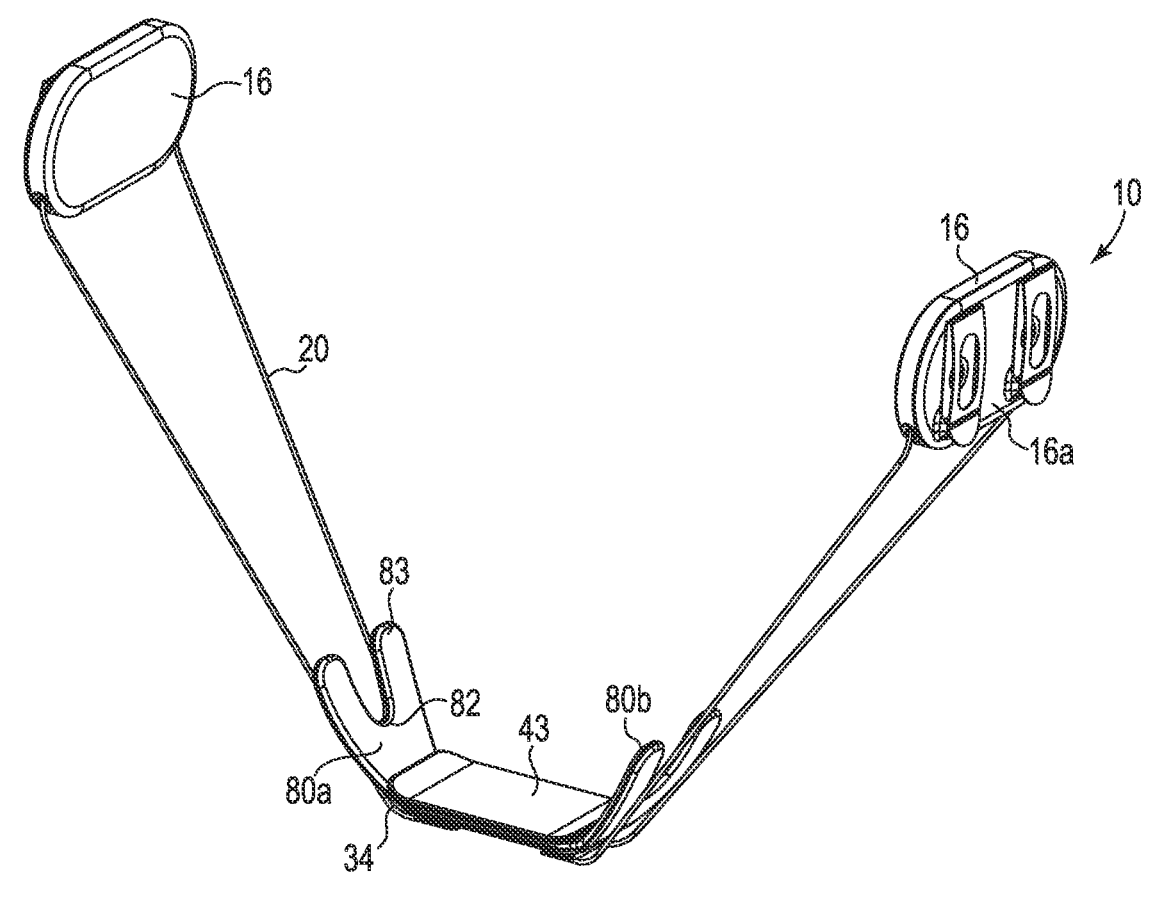
Fig. 21
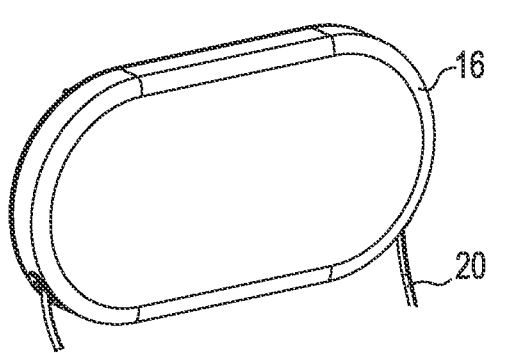
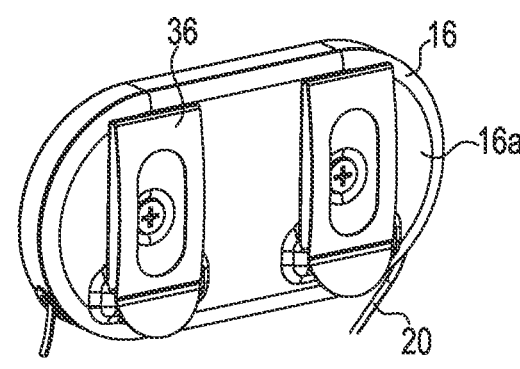
Fig. 22              Fig. 23

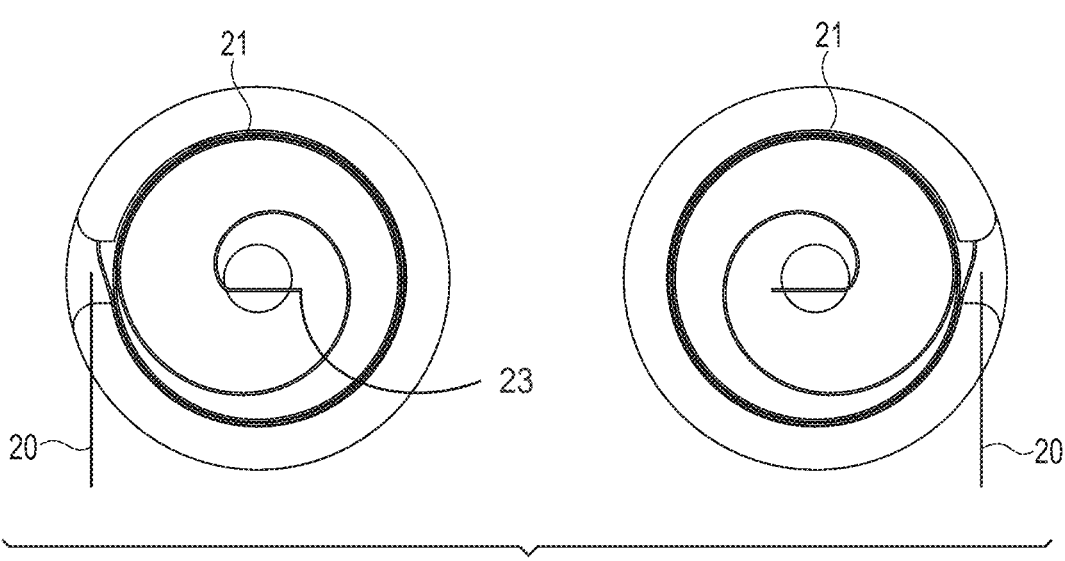
Fig. 26
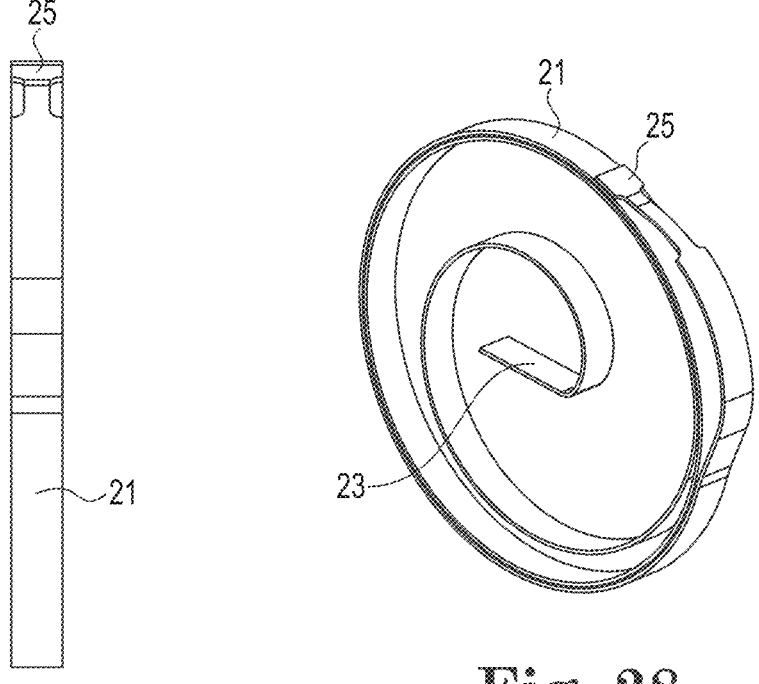
Fig. 27
Fig. 28

WEARABLE PERINEUM LEAKAGE CONTROL DEVICE

PRIORITY

This patent application claims priority to and the benefit of U.S. Provisional Patent Application No. 63/182,335, filed Apr. 30, 2021, which is incorporated fully herein by reference.

FIELD

The present invention relates to external incontinence control devices and methods, and more particularly to external perineum leakage control devices and methods that are able to control involuntary liquid discharges or leakages from the orifice(s) of a user's perineum.

BACKGROUND

Millions of people suffer from involuntary leakage or discharge of bladder, vaginal, and bowel fluids. This involuntary leakage, termed incontinence, can be very upsetting to those suffering with the condition. It is not uncommon for sufferers to limit their social interactions as a means of attempting to avoid potentially embarrassing situations caused by their involuntary leakage. People suffering from involuntary leakage suffer from higher incidence rates of depression and anxiety. It is particularly troubling for the aging portion of a population.

Involuntary leakage generally occurs from the lumens or openings associated with the urethra, vagina and rectum. Urinary incontinence is the result of urine leaking out of the urethra from the urinary system, which consists of the kidneys, ureters, bladder and urethra. Vaginal leakage or discharge is often the result of a user's menstrual cycle or an infection. The discharge leaks from the vaginal opening of the reproductive system, which includes the uterus, ovaries, and vagina. Lastly, fecal incontinence occurs when fecal matter escapes from the rectum, which is part of the digestive system, which consists of the stomach, small intestine, large intestine, and the rectum.

Various methods and external devices for preventing, alleviating, and absorbing leakage and discharges from the openings in the user's perineum region are currently available. A wide variety of these devices accomplish their intended result by placing and keeping disposable articles, such as pads, sanitary napkins, liners and the like in close contact with the opening(s) or orifice(s). These devices use adhesive for the article's attachment to a user's undergarment. Example articles are described, for example, in U.S. Pat. No. 4,337,772, which keeps the absorbent articles in close contact with the openings by using an adhesive on their backing to secure them to the user's undergarment. These devices were not intended to inhibit or stop leakage from the orifice but rather to capture and collect the leakage from leaking beyond the article or device.

The efficacy of traditional methods and devices is heavily dependent upon several factors, including the proximity of the absorbing article to the opening(s) or orifice(s), the means of attachment to the undergarments or user's skin, and the material used to contain or retain the leaked fluids/material. As described above, most disposable articles are held in place during use by attaching them to the user's underwear or undergarment (in the case of pads or liners). To this day these traditional absorbent articles have several shortcomings, including movement within or upon the undergarment, which allows leaked fluids to travel into and through the undergarments. They also suffer from a lack of capacity, where once the article is full of the leaked fluid it begins to overflow into and through the user's undergarment.

Other external non-absorbing devices have also been developed. These non-absorbing occlusive devices include those described in U.S. Pat. Nos. 6,056,687 and 9,408,684B2. The non-absorbing occlusive devices, like the absorbent devices, typically use adhesives to attach or secure them to the user's skin around the opening of the orifice that is leaking. For example, they will use an adhesive that is adhered to the skin around a user's urethra in an attempt to prevent and/or capture leaking urine. These non-absorbing occlusive devices, however, suffer from several shortcomings, including allergic reactions to the adhesive and/or device, and painful removal of the device due to their use of an adhesive on sensitive vaginal tissue.

Non-adhesive devices were developed to overcome some of the shortcomings of the other adhesive devices. For instance, urethral cups such as those disclosed in the U.S. Pat. Nos. 5,885,204 and 5,989,180, were developed utilizing atmospheric pressure to create a vacuum in order to maintain or retain the urethral cup in a position over the female urethral opening. However, these devices were not successful due to the vacuum mechanism drawing fluid out of the urethra, which then required frequent emptying and superficial tissue bruising (caused by the vacuum) proximate to the attachment site of the device.

As a result of the shortcomings of the above devices, sufferers often revert back to the use of absorbable garments such as disposable/washable/reusable pull-on garments such as adult diapers. These adult diapers are generally tight-fitting pull-on garments such as those described in U.S. Pat. No. 4,813,950, which act as a girdle to ensure the article's proper positioning and close contact with the openings in the user's perineum.

Applying and removing the labial pads with adhesive and vacuum cups are a challenging exercise for the majority of users. An improperly placed pad or cup does not prevent leakage. Many women are averse to the use of body adhesive. When the adhesive portion of the device comes into contact with any hair in the region, such as pubic hair, removal of the device can be painful. Using disposable adhesive coated labial pads is prohibitively expensive for many consumers as the used pad needs to be replaced with a new one after each voiding or upon reaching the capacity of the pad.

The attachment force of vacuum and adhesives is not capable to prevent displacement of the devices during sporting activities (especially when they get wet) and during urinary stress incontinence episodes. Adhesives do not resist moisture. Moreover, all the above devices are not capable to return to their original position, after being shifted away by the user's bodily movements.

Other devices, such as those described in U.S. Pat. Nos. 3,608,551 and 5,611,722 suggest using elastic components in the leakage protecting garments for uplifting, thereby enabling better and stable positioning of the sanitary articles against the openings in the user's perineum and for improved discretion.

Still other devices, such as those described in U.S. Pat. No. 9,314,382 B2, describe methods of applying localized pressure to the perineal opening(s) through articles in order to compress the orifice(s) of a user to prevent involuntary bodily leakages or discharges. Such compression may be exerted by wearing tight fitting pull-on underwear, by use of sanitary belts, or by using thong-shaped holders, all of which are designed with upward pushing elastic components that uplift, support, and compress the articles against the leaking opening(s). Such devices are anchored to the user's elastic waistband or are adhesively secured to either the crotch portion of a garment, the device itself, or to the user's skin. One of the challenges with using elastic materials to apply an upward compression force is that the force applied is not constant and depends on how far the elastic materials are extended resulting in variable force being applied depending on the user's shape and vigorous bodily movements. Therefore, these devices performance for leakage prevention is highly dependent on a user's shape or activity level.

The use of belts to secure an article in position against the opening is described in U.S. Pat. Nos. 6,632,210 and 9,913,747. A part of the belt is described as compressing in the user's gluteal cleft. Thong-shaped holders are described in U.S. Pat. No. 8,454,570, which teaches how a thong-shaped holder may keep an article in close bodily contact to the user's pudenda. According to the invention, the user's waistband, front, rear, and crotch parts are elasticized. When these components are stretched by the user's body, they exert upward compressive forces against the article, which keeps the article in close contact with the user's pudenda region.

Specially designed tight-fitting undergarments are deemed by many users to be binding and uncomfortable to wear, especially during vigorous body movements. The function of the conventional pads is to absorb urinary emissions. They reduce neither the leakage amount during the incontinence episodes nor the frequency of incontinence episodes.

The above existing devices all suffer from various drawbacks. They all suffer from one or more of the following: being bulky, moving causing leaks, variable performance depending on the user's shape or size, uncomfortable to wear, being visible through a user's outer clothing, and other failures that allow leakage to occur past or beyond the device.

There exists a need for a novel device that prevents or mitigates leakage out of the orifice(s). There is also a need for a device that is comfortable, easy to use, and is not visible through a user's outer garments.

There exists a need for a device that is able to accommodate users having different anatomical shapes, sizes, and other anatomical differences, including but not limited to variations in the location of their urethral, vaginal, and rectal orifices, and the topography of such anatomical locations.

There is yet also a need for an effective mechanism to secure an occluding device in a desired anatomical position or location that will not materially shift during the user's dynamic body movements. Forces associated with bodily movements such as walking, running, bending, sitting, and exercising, etc. often overcome the retaining forces of the traditional devices.

There is also a need for a device that includes a waistband that will not slip or slide down causing dislodgement or displacement of an occluding member.

There is another need for a device that balances the need to apply enough pressure to the urethral meatus to help prevent or mitigate leakage with the need to not apply too much pressure such that it results in vesicoureteral reflux where excess pressure causes urine to go back up to the kidneys which can result in reflux nephropathy over time.

Furthermore, there is a need for a device that enables easier placement of a pad against the urethral meatus. Elderly individuals are substantially more likely to suffer from incontinence and many elderly individuals sometimes lack the manual dexterity and coordination to place a pad against the urethral meatus without assistance.

Such shortcomings are resolved by the various embodiments of the present invention.

SUMMARY OF THE INVENTION

In response to the needs discussed above, the present invention provides a method and an external device to control leakages of bodily fluids and discharges from the openings of lumens in the user's perineum region. In an example embodiment of the present invention, the disclosed device controls female urinary incontinence. However, the present invention is also able to control fecal incontinence and vaginal disorders such as vaginal discharge and vaginal prolapse.

In one example embodiment of the present invention, a leakage control appliance or device generally comprises of one or more retractors or retraction mechanisms coupled to one or more band or bridge members with the one or more retraction mechanisms configured to apply a pulling force onto the one or more band or bridge members. The pulling force or forces keeps the one or more band or bridge members against the opening(s), thereby increasing a perineum pressure that is greater than a bladder pressure. This pressure differential prevents or mitigates fluid or discharge leakages. In some example embodiments of the present invention, the one or more band or bridge members comprise an absorbent component that is configured to absorb any leakage or discharge that may happen to escape.

In one example embodiment, the leakage control appliance or device comprises front and rear retractor or retraction mechanisms, a slider assembly (including the band or bridge member), which connects the front and rear retractor or retraction mechanisms, and a disposable sanitary article or absorbent member attached to the slider's bridge member. Each of the front and rear retraction mechanisms includes a rotatable spool driven by a constant force spring and has a flexible cord(s). The cord(s) is connected to and wound on the spool. The spool and spring retracts, rewinds, and tensions the connected cord(s) when the said cord(s) are pulled out. The cords' tension force is equal to the combined retraction forces of all coil springs in the front and rear retractors or retraction mechanisms and remains predetermined and constant regardless of the distance the cord(s) are pulled out and regardless of the related deflection of the reels' springs. The cord(s) of the front and rear retraction mechanisms have components to connect them to the front and rear retraction mechanisms of the slider, which may comprise front, rear, and middle (crotch) sections. A disposable article, such as an incontinence pad, may be attached to the slider's bridge member by a fastener or securing mechanism such as a snap, hooks and loop fastener or adhesive. The front and rear retraction mechanisms may also have a fastening component, such as a clamp, hook and loop fastener, or snap, to attach the retraction mechanisms to the front and rear of a user's undergarment waistband.

When a user puts on an undergarment with the attached leakage control device and positions the slider and pad against the leaking orifice (e.g., urethral orifice), the front and rear cord(s) become pulled out and the retracting reels or spools tension the cord(s), exerting a constant and predetermined upward compression force to the slider's bridge member and the attached article or absorbent member. The predetermined compression force keeps the slider's bridge member in constant close contact with the user's pudenda region. By pressing the article against the pudenda openings, it prevents leaks when bladder pressure is at or below a predetermined level. Additionally, it mitigates and absorbs involuntary and transient leaks when bladder pressure is above a predetermined level. The predetermined pressure is selected to be below a certain threshold to avoid the risk or vesicouretral reflux where excess pressure causes urine to go back up to the kidneys resulting in reflux nephropathy over time.

Due to the retraction mechanisms' constant retraction force the article remains in constant close proximity with the opening(s) and the leakage control device controls leakages regardless of a user's vigorous bodily movements or movement a user's undergarment waistband. The leakage control device is also adjustable to all body shapes and sizes. To allow voluntary unrestricted regular micturition, a user simply pulls down their undergarment with the attached leakage control device. To replace the soiled article, the user removes the article from the slider's bridge member and snaps or adheres a new one to the bridge member.

The invention encompasses embodiments, which control leakages from a user's urethral, vaginal, and anal openings while also allowing drainages when desired. Numerous other features and advantages of the present invention will appear in the following description in which reference is made to exemplary aspects of the invention.

BRIEF DESCRIPTION OF THE DRAWINGS

The device of the present invention (hereinafter, "device") is described in detail below with reference to examples of preferred embodiments illustrated in the accompanying drawings. The invention may be developed in multiple embodiments, with all sharing key design features such as use of "retraction mechanisms" (which may be spring-loaded tensioners as shown in the drawings or otherwise motorized retraction mechanisms) to secure the device to the user's perineum region.

FIG. 21 is a perspective view of an example embodiment of the leak control device;

FIG. 22 is a perspective view of a front surface an example retraction mechanism of the present invention;

FIG. 23 is a perspective view of a back surface an example retraction mechanism having clips of the present invention;

FIG. 26 is a front view of example power springs or retractor members of the present invention;

FIG. 27 is a side view of an example power spring or retractor member of the present invention;

FIG. 28 is a perspective view of example power spring or retractor member of the present invention;

DETAILED DESCRIPTION OF THE INVENTION

The accompanying drawings illustrate a method and example embodiments of a leakage control device, appliance, and method to control involuntary leakages (e.g., bodily discharges such as urine and feces) from openings of the pelvic lumens. The pelvic lumens include the urethra, vagina, and rectum or anus. The pelvic lumens are generally located in the perineum region of a female user. While the invention will be described in use with a female, it is contemplated herein that the device of the present invention can also be used with the male anatomy.

It will be apparent to those skilled in the art from this disclosure that the following descriptions of examples of embodiments are provided for illustration only and not for any purpose of limiting the invention or substantially identical embodiments thereof. Multiple embodiments are possible for key invention concepts such as the use of retraction mechanisms for securing the various potential embodiments of the device. The invention may be varied in construction and details without departing from its scope, and the overall idea of using retraction mechanisms to control leakage of bodily discharges from openings in the user's or user's perineum region.

Figure 1:
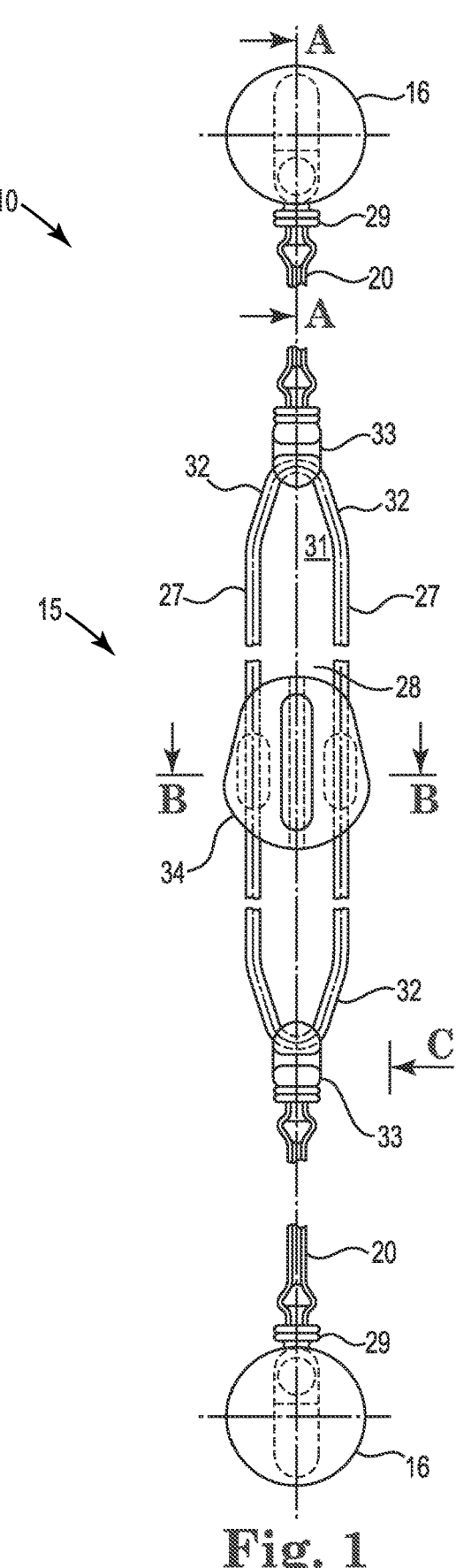
FIG. 1 is a top view of an example embodiment of the leak control device.
Figure 2:
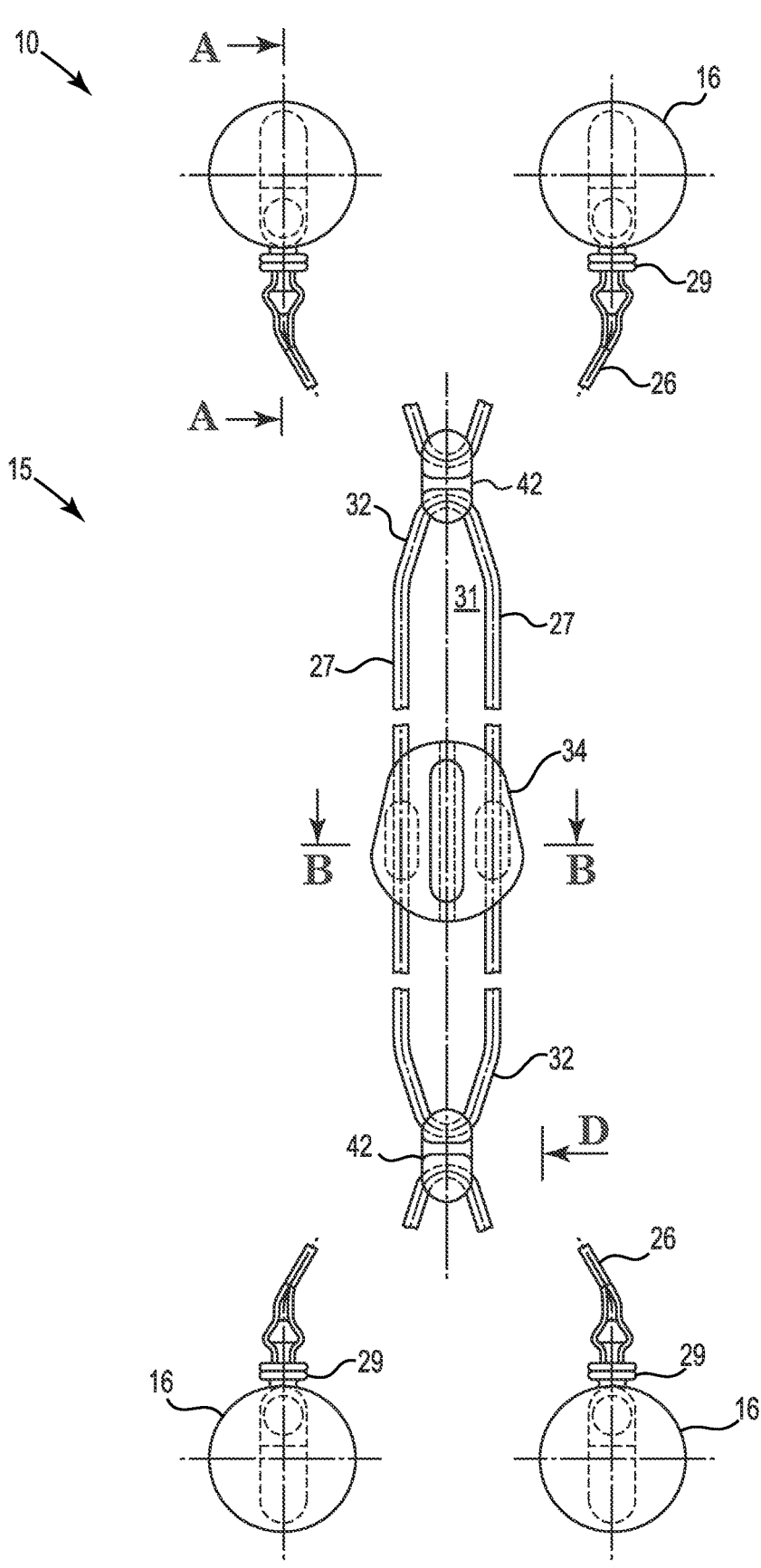
FIG. 2 is a top view of an example embodiment of the leak control device.

Referring now to the drawings, FIGS. 1 and 2 illustrate top views of example embodiments of a wearable perineum leakage control device or appliance 10. As particularly illustrated in FIGS. 3-7, the wearable leakage control device 10 comprises an externally worn active harness assembly 15 to control leakage of bodily discharges from openings in a user's or user's perineum region.

Figure 3:
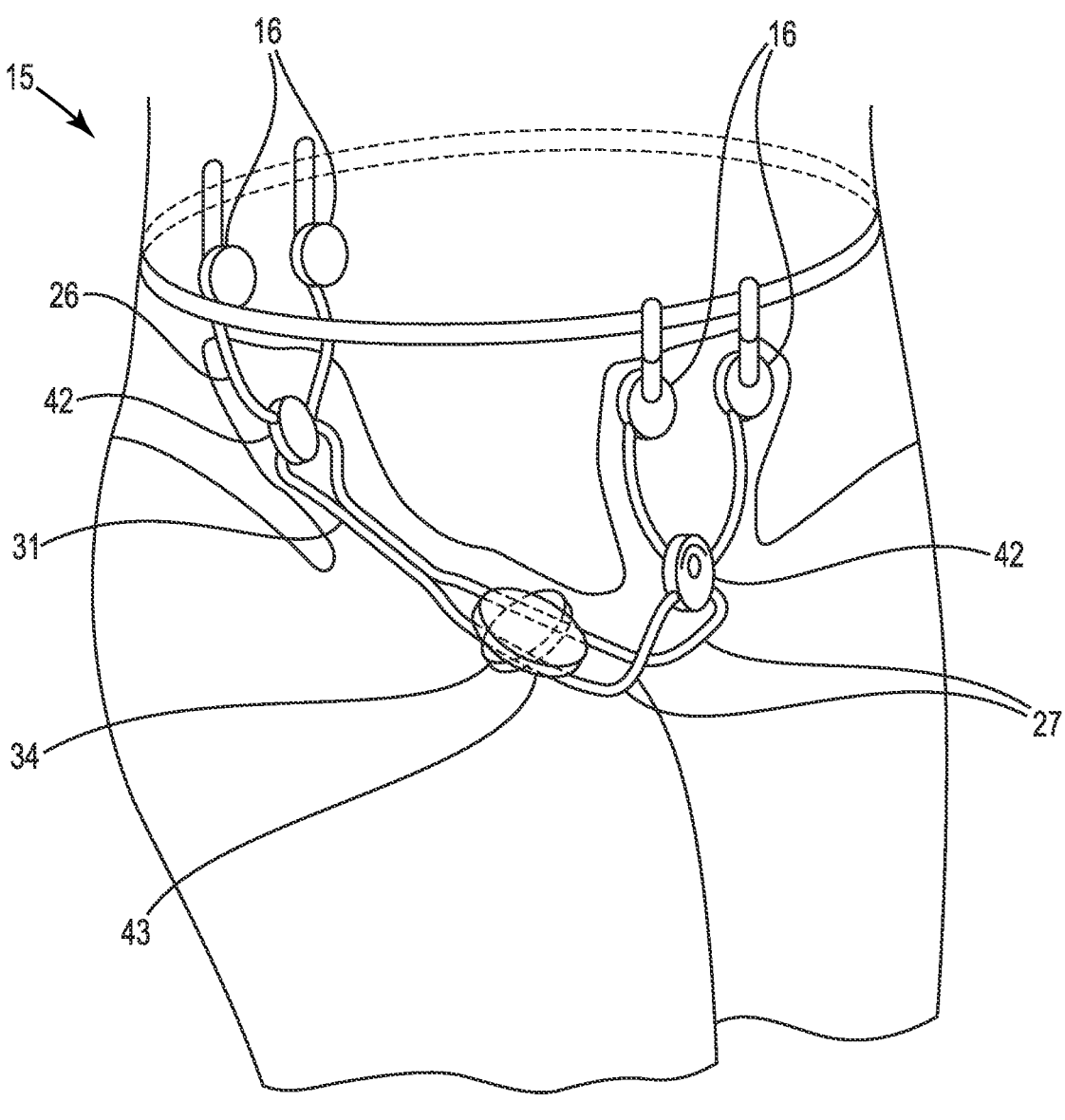
FIG. 3 is a perspective view of an example embodiment of the leak control device as attached to a user's underwear.

As illustrated in FIG. 3, the harness assembly 15 comprising one or more retractors or retraction mechanisms 16 worn proximate to the waist of a user. Each of the retractors or retraction mechanisms 16 includes a retracting member or cord 20 retractably coupled to it that can be adjustably coupled to a slide assembly or bridge member 34. In some example embodiments of the present invention, as discussed in more detail below, one or more intermediate support members 26 and/or end support members or straps 27 can be coupled to the retracting member or cord 20 and the bridge member 34. As will be discussed in more detail, the intermediate support members 26 and/or end support members or straps 27 provide additional functionality and configurations of the leakage control device 10.

The retractor or retraction mechanism 16 is actively coupled to a retracting member or cord 20, and if present, the retracting intermediate support member 26 and/or support members 27. The retracting member or cord 20, and if present, the retracting intermediate support member 26 and/or support members 27 extend between the retraction mechanism 16 and undergarment, or between two retractors or retraction mechanisms 16, and pass over the perineum region of the user. The retraction mechanism 16 is configured to pull or retract the retracting member or cord 20, and the intermediate support members 26 and/or support members 27, if present. The retraction force of the retractor or retraction mechanism 16 applies a compressive force against one or more areas of the perineum, causing an increase in perineal pressure. The perineal pressure counteracts a bladder pressure, thereby preventing or mitigating leakage.

Figure 8:
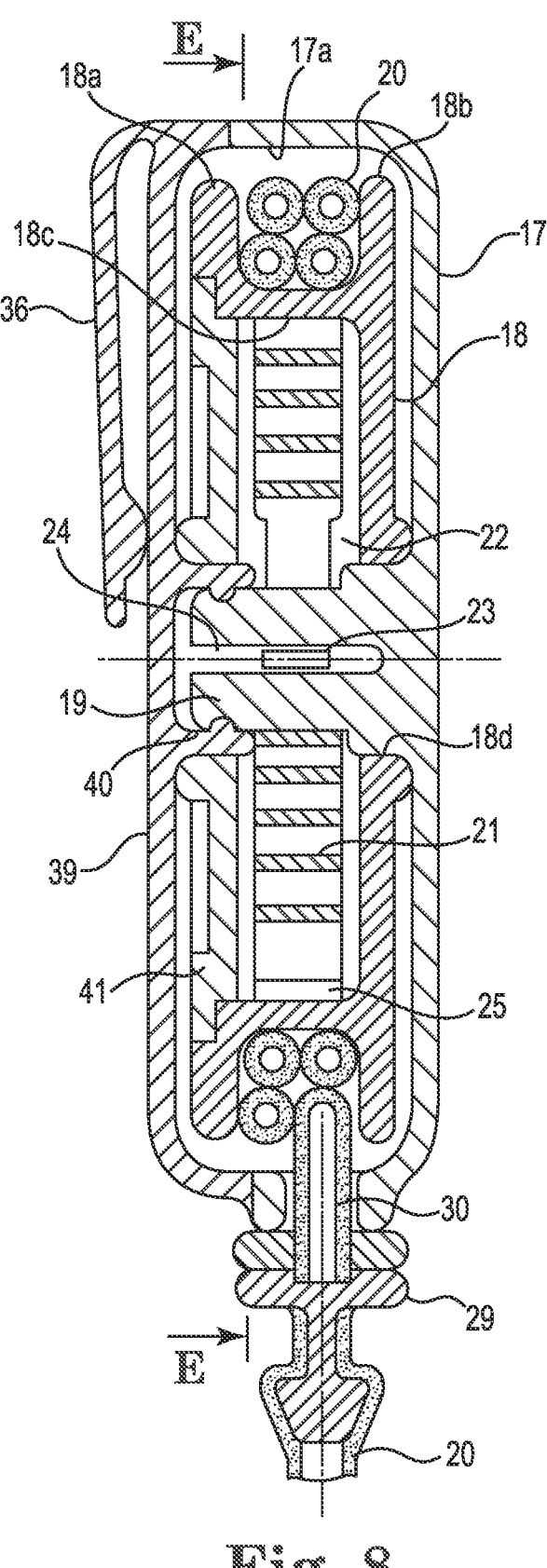
FIG. 8 is cross-sectional view along line A-A of FIG. 1.
Figure 9:
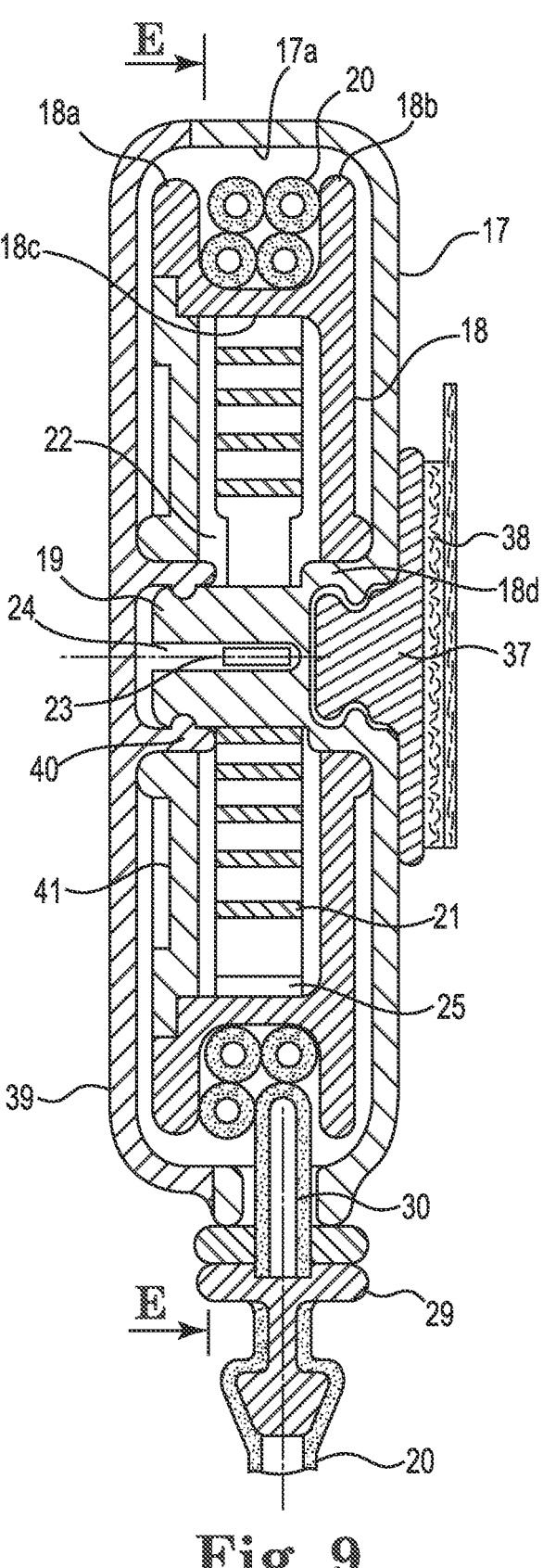
FIG. 9 is cross-sectional view along line A-A of FIG. 2.
Figure 13:
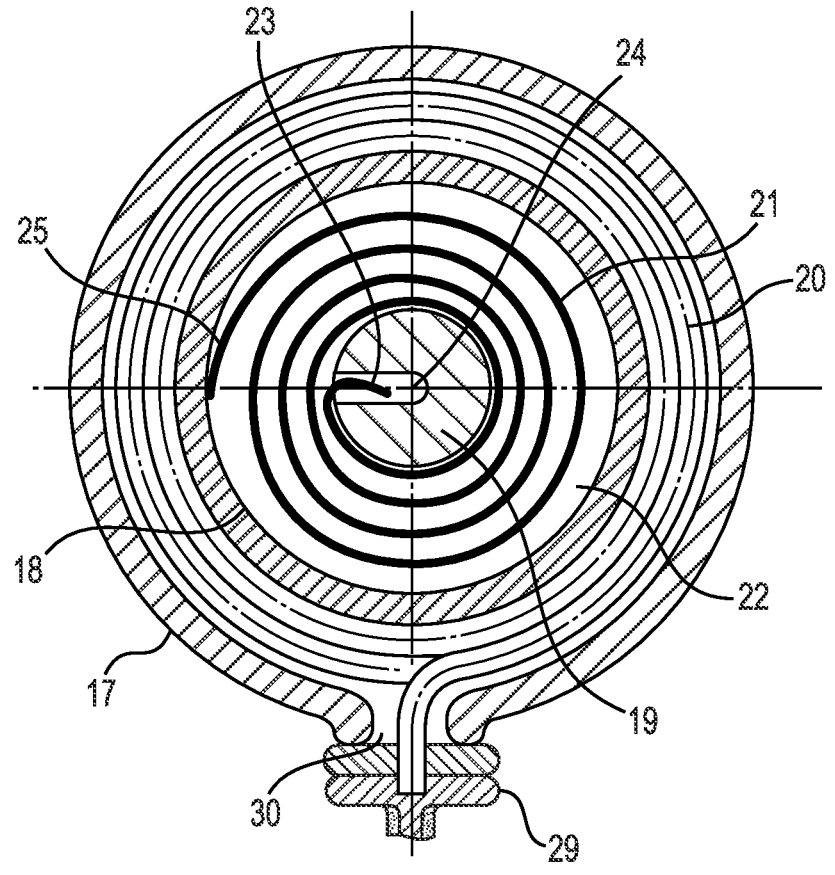
FIG. 13 is a cross-sectional view along lines E-E of FIG. 8 and FIG. 9.
Figure 14:
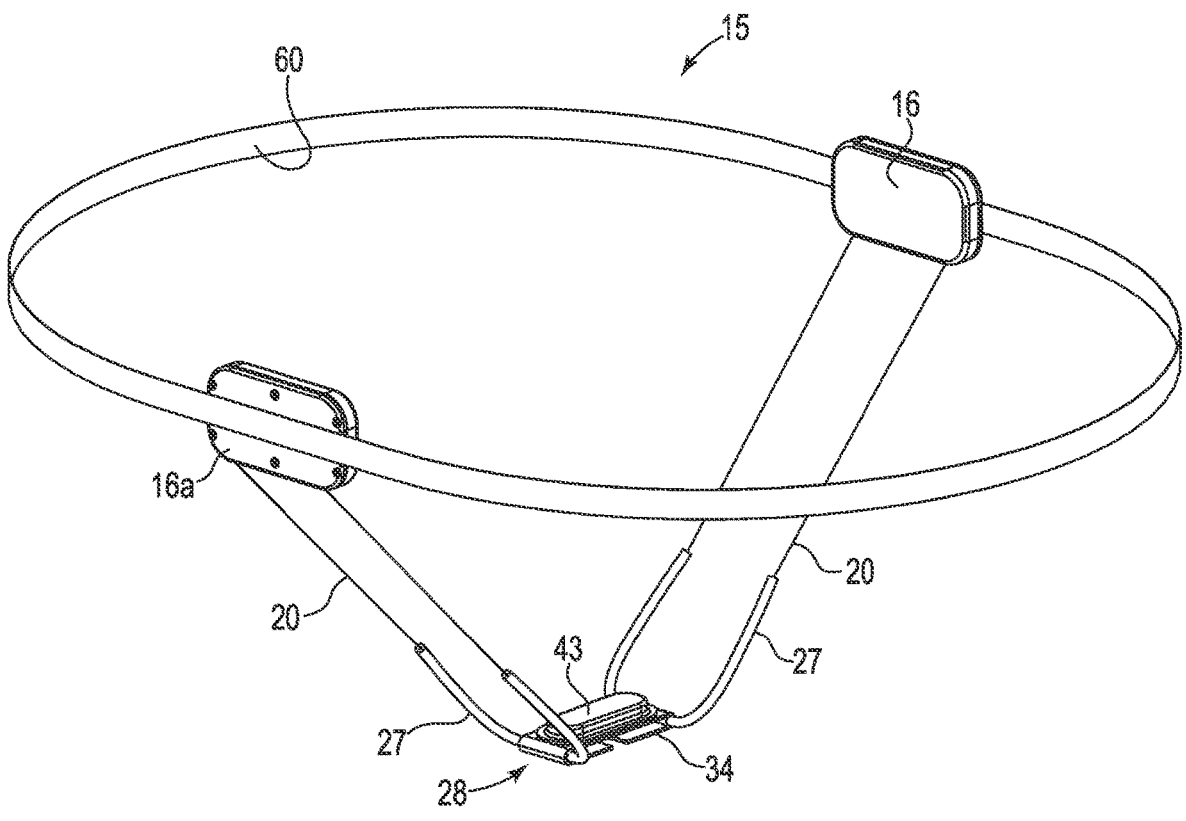
FIG. 14 is a perspective view of an example embodiment of invention.
Figure 15:
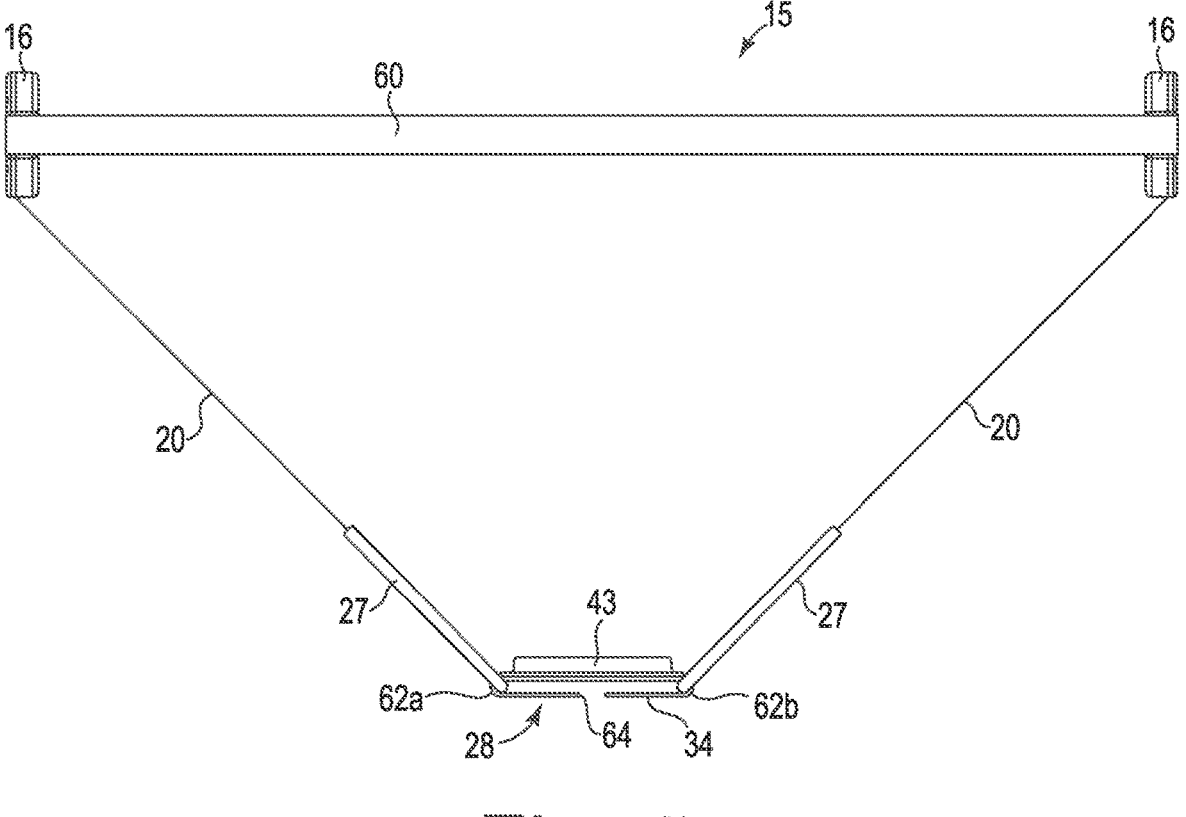
FIG. 15 is a side view of an example embodiment of the present invention.
Figure 16:
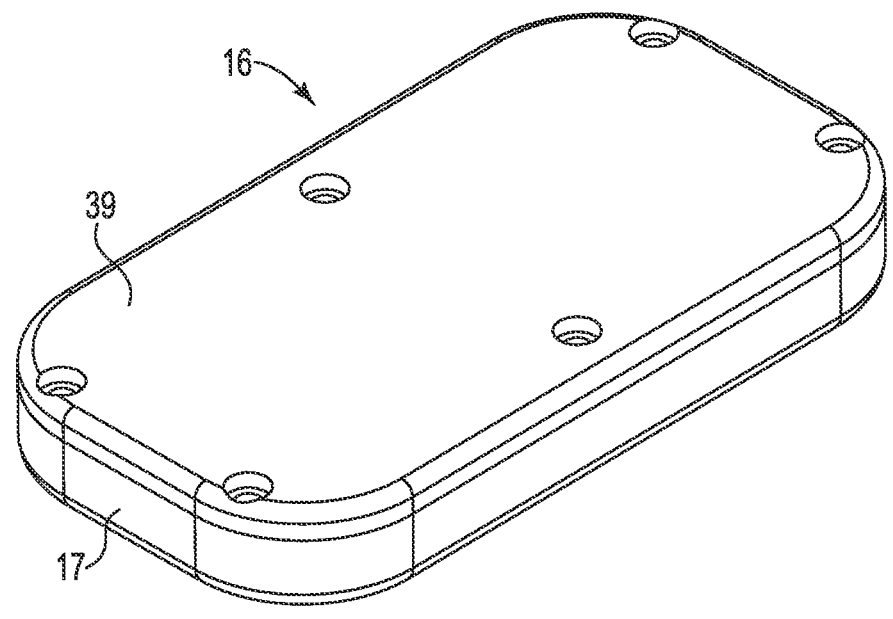
FIG. 16 is a perspective view an example retraction mechanism of the preset invention.
Figure 17:
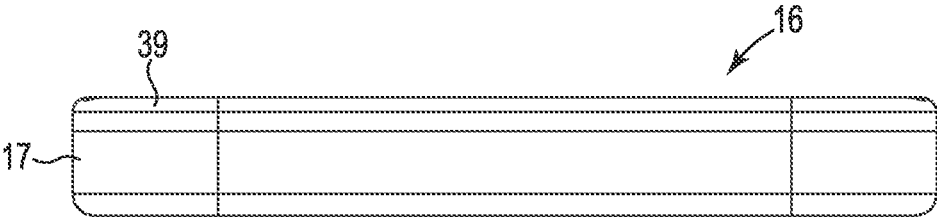
FIG. 17 is a side view of an example retraction mechanism of the preset invention.
Figure 18:
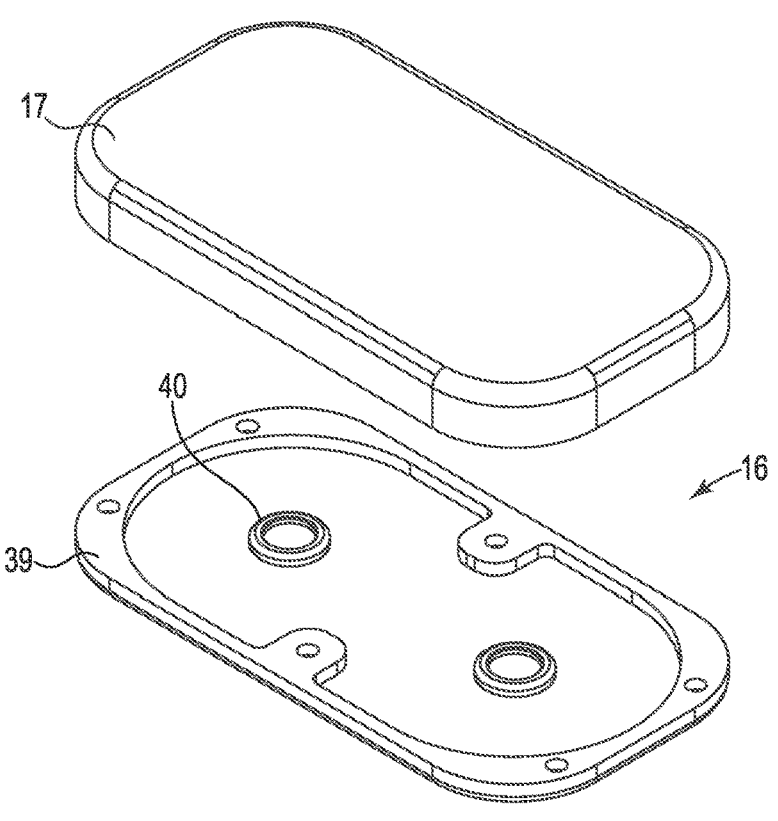
FIG. 18 is an exploded view of an example retraction mechanism of the present invention.
Figure 19:
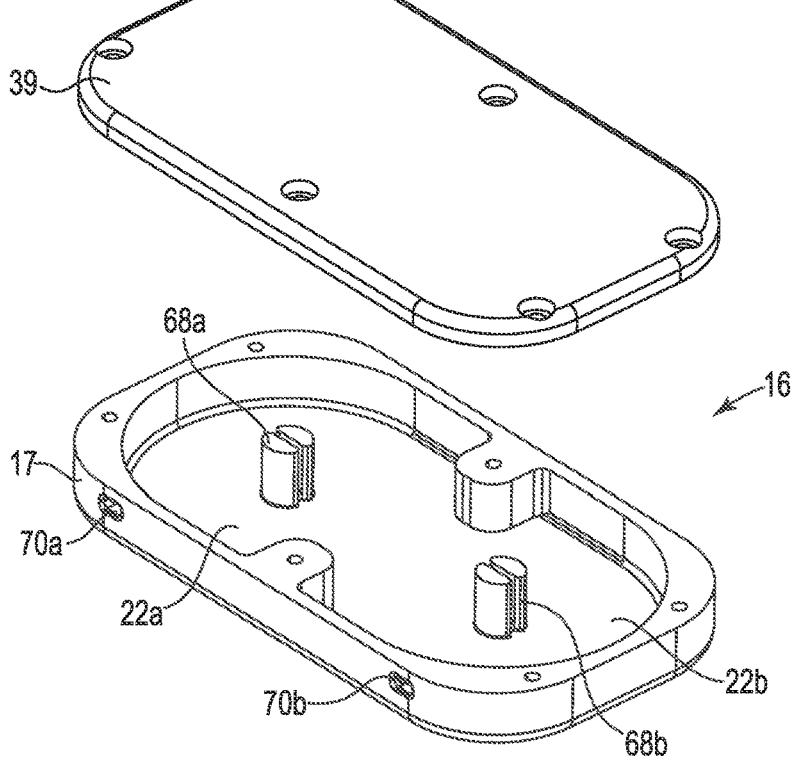
FIG. 19 is an exploded view of an example retraction mechanism of the present invention.
Figure 20:
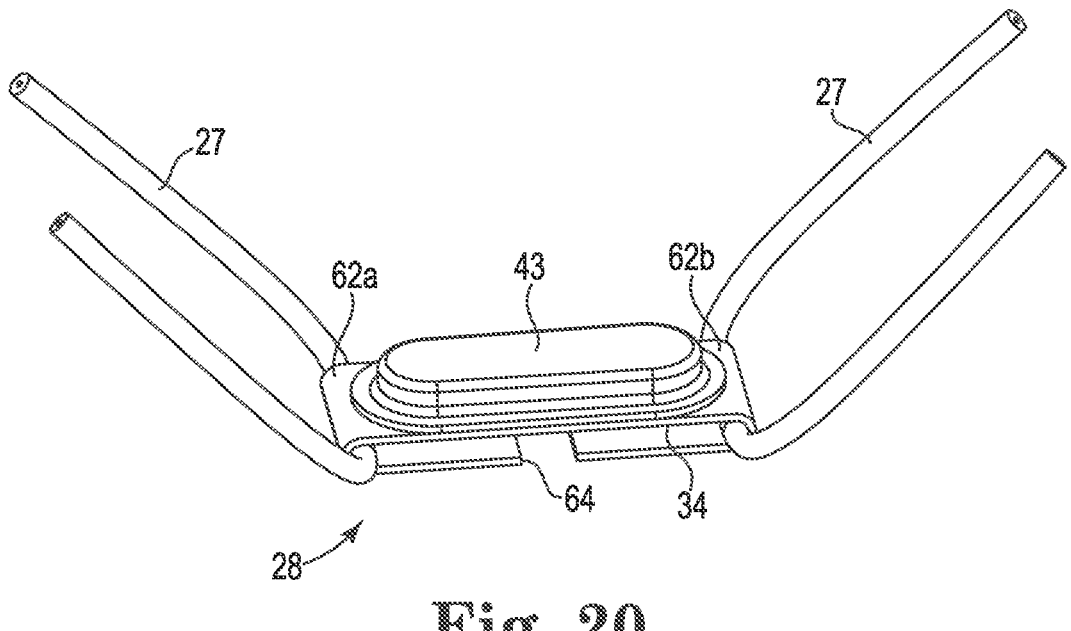
FIG. 20 is a perspective view of an example slider of the present invention.

As shown on FIGS. 8, 9, and 13, each retractor or retraction mechanism 16 comprises a housing 17 having an interior 17a. The interior 17a of the housing 17 contains a spool 18 that is supported in a rotatable state on a shaft or post 19 contained in the housing 17 and extending through a portion of the interior 17a. The spool 18 has a generally annular shape comprising generally spaced apart lips or flanges 18a and 18b, extending from a barrel 18c having an axially extending bore or opening 18d that is adjustable and positionable over and in rotatable communication with the post 19. The retracting member or cord 20 is wound on or about the spool 18 between the spaced apart flanges 18a and 18b.

In an example embodiment of the present invention, as particularly illustrated in FIGS. 8 and 9, the spool 18 includes a central interior cavity 22 configured to house a biasing member or spring 21 that is configured to apply a constant and predetermined pulling force on the retracting member or cord 20. The biasing member or spring 21 is coupled to or in contact with a portion of the spool 18 and/or a portion of the post 19, wherein it is able to move the spool 18 and the retracting member or cord 20 from an uncoiled state to a coiled state, or from an extended state to a retracted state.

In one embodiment of the present invention, the biasing member or spring 21 comprises a constant force spring mounted or positioned in the central interior cavity 22 of the spool 18. The biasing member or spring 21 includes an inner end 23 that is coupled to, in contact with, or mates with a portion of the post 19. A slot 24 may be formed on or in the shaft of the post 19 to receive and retain the inner end 23 of the biasing member or spring 21. The biasing member or spring 21 also includes an outer end 25 that is tethered on, positioned against, or coupled to a portion of the spool 18. In an example embodiment, an inner surface of the barrel 18c of the spool 18 may comprise a slot, lip, ridge, or fastening mechanism that is configured to retain the outer end 25 of the biasing member or spring 21 in contact with the spool 18.

In another example embodiment of the invention, the biasing member or spring 21 may comprise a spiral torsion spring that is configured to provide a constant and predetermined tension or force. Other biasing members or springs 21, mechanisms, or configurations are also possible and should be considered to be within the spirit and scope of the invention.

The biasing member or spring 21 is configured to store energy created when the retracting member or cord 20 is pulled or extended out of the housing 17, which applies constant and predetermined force/torque to the spool 18, thereby causing the pulled-out retracting member or cord 20 to automatically retract and rewind on the spool 18. The constant and predetermined retracting force is applied to the slider or bridge member 34 that extends along or across the perineum. The constant and predetermined force imparts pressure against the perineum stopping the leakage.

In one example embodiment of the invention, using end support members or straps 27 coupled to the retracting member or cord 20 wound about the spool 18. As the spool 18 automatically moves to the wound or coiled state it pulls on the retracting member or cord 20 and the end support members or straps 27. The end support members or straps 27 press against bridge member 34, which presses against the perineum causing an increase in the perineal pressure that overcomes the bladder pressure, and thereby prevents or mitigates leakage.

In another variation of the present invention, the retracting member or cord 20 includes one or more adjustment portions or intermediate support members 26 extending outside of the housing 17 and interconnecting the retracting members or cords 20 with the end support members or straps 27. The intermediate support members 26 and end support members or straps 27 may be composed of the same or different materials.

As briefly mentioned above, a bridge member or assembly 34 can be connected or coupled to the retracting members or cords 20 or the end support members or straps 27, if present. The bridge member 34 enables a user to more precisely direct the applied pressure to the perineum. It also enables a user to adjust the location or position of the bridge member 34 for their anatomy.

The constant and predetermined tension force of the biasing member or spring 21 is generally equal to the constant and predetermined force applied along the retracting member or cord 20, intermediate support members 26, the end support members or straps 27, and the bridge member 34. The force remains constant regardless of the length or amount of the retracting member or cord 20 extending of the housing 17. The constant and consistent force of the retractor or retracting mechanism 16 ensures the leakage control device 10 is effective and safe to operate. Applying an acceptable level of pressure is important because if the pressure is too high it may increase the risk of vesicouretral reflux (where urine goes back up to the kidney causing kidney damage over time (reflux nephropathy)) and if the pressure is too low it may allow leakage.

In the example embodiment of FIGS. 8 and 9, a stopper or plug 29 is coupled to the retracting member or cord 20 to limit or stop the retracting member or cord 20 from retracting completely into the interior 17*a* of the housing 17. In another example embodiment, the stopper or plug 29 is coupled to and extending between the retracting member or cord 20 and the intermediate support member 26 to prevent the intermediate support member 26 from entering the interior 17*a* of the housing 17. The plug or stopper 29 also acts to seal a dispensing opening 30 in the housing 17. A distal end of the retracting member or cord 20 can be tethered or coupled to the spool 18 to prevent the retracting member or cord 20 coming completely out of the housing 17.

Referring to FIGS. 1 and 2, the end support members or straps 27 can form a generally loop shape or configuration with the end support members or straps 27 being generally parallel and forming generally opposed arched ends 32. The opposite or opposed arch ends 32 can be detachably connected by connectors 33 and 42 that connect with proximal ends or a portion of the intermediate support members 26 as depicted by FIGS. 1, 2, 11 and 12.

Figure 10:
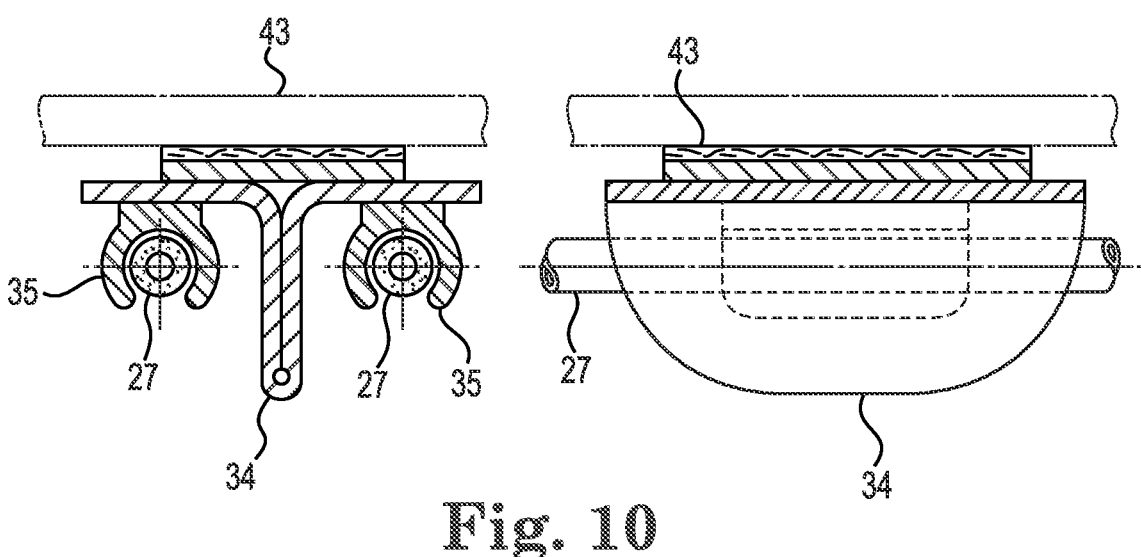
FIG. 10 is a cross-sectional view along lines B-B of FIG. 1 and FIG. 2, respectively.
Figure 11:
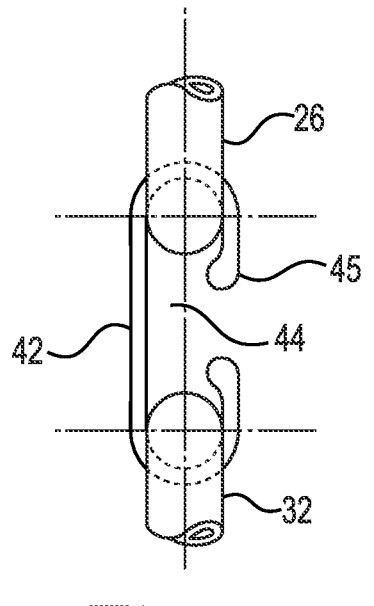
FIG. 11 is a side view along line C of FIG. 1 illustrating an example detachable connector used for connecting straps of example embodiments of the leak control device.
Figure 12:
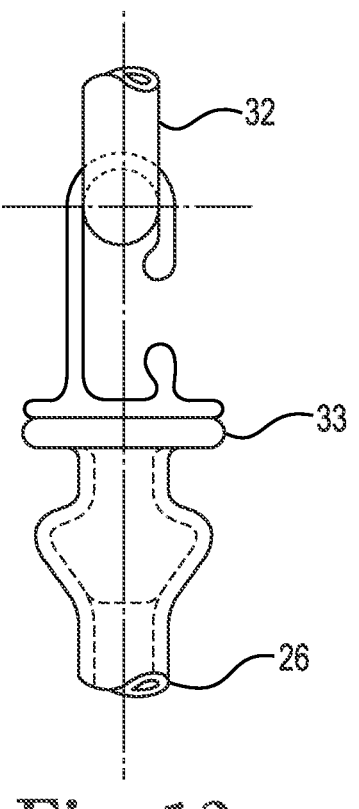
FIG. 12 is a side view along line D of FIG. 2 of an example detachable connector used for connecting straps of example embodiments of the leak control device.

In one example embodiment of the present invention, the bridge member 34 is part of a slide assembly 31 adjustably coupled to and movable along the end support members or straps 27. As particularly illustrated in FIG. 10, the flexible bridge member 34 of the slide assembly 31 is coupled to the end support members or straps 27 by one or more connectors 35 extending from a lower surface of the bridge member 34 and mating with a portion of the end support members or straps 27. The connectors 35 are configured to slide along and removably connect the flexible bridge member 34 to the two parallel end support members or straps 27. The movement of the bridge member 34 along a length of the end support members or straps 27 enables a user to adjust the properly position the bridge member 34 to their anatomy.

The leakage control device 10 may include one or more fastening member or component(s) 36 to secure, attach, or couple the leakage control device 10 on the waistband of the users' undergarments or other portions of a users' garments. In the example embodiment of FIG. 8, the fastening member or component(s) 36 may comprise a hook or clip member that can be slid or fit over a band or waistband of a users' clothing.

Referring to FIG. 9, the fastening member or component(s) 36 may also comprise a coupler 37 that is able to engage or mate with a portion of the housing 17. The coupler 37 may comprise a snap or other fastener that is coupled to a user's undergarment or a snap or other fastener that pinches or sandwiches a portion of the users' undergarment between portions of the fastener. The fastening member or component(s) 36 may also comprise an adhering member 38, such as an adhesive or a hook and loop fastener, as shown in FIG. 9. Any fastening member or component(s) 36 may be used and may be permanent or detachable. Additionally, any combination of fastening component(s) 36 may be employed to secure or fasten the leakage control device 10 in place.

In order to repair or replace components of the leakage control device 10, the housing 17 may comprise one or more covers 39 that provide selective access to the interior cavity 22 of the spool(s). The one or more covers 39 are configured to couple to or fasten to another portion of the housing 17. In one example embodiment, the one or more covers 39 comprise a coupling arrangement such as a hollow bushing

40 that mates with the post 19. The coupling arrangement or bushing 40 is also able to support at least a portion of the rotatable spool 18. Fasteners such as screws may also be used to secure the one or more covers 39 to the housing 17. The fasteners may extend through and be coupled to a portion of the post 19.

The internal cavity 22 of the spool(s) 18 may also contain one or more covers, doors, or seals 41 to protect the biasing member or spring 21. The one or more doors 41 can include one or more sealing members capable of retaining a lubricating material inside of the internal cavity 22, which is used to extend the life of the biasing member or spring 21. The one or more doors 41 can be secured to a portion of the spool 18 by any type of clipping mechanism or fastener.

Turning to another example embodiment of the invention, FIG. 2 illustrates the leakage control device 10 having two or more opposed retraction mechanisms 16 with each retraction mechanism 16 being coupled together by either a single retracting member 20 or an intermediate support member 26 being coupled to ends of the retractor member or cord 20 of each retractor or retraction mechanism 16. As particularly illustrated in FIG. 11, each intermediate support member 26 is coupled to a connector 42 that is also coupled to ends 32 of the end support members or straps 27. The connector 42 can be manufactured having one or more side openings 45, which allows one to press and lodge the cord 26 and/or ends 32 of the end support members or straps 27 into a longitudinal cavity 44 of the connector 42.

Figure 4:
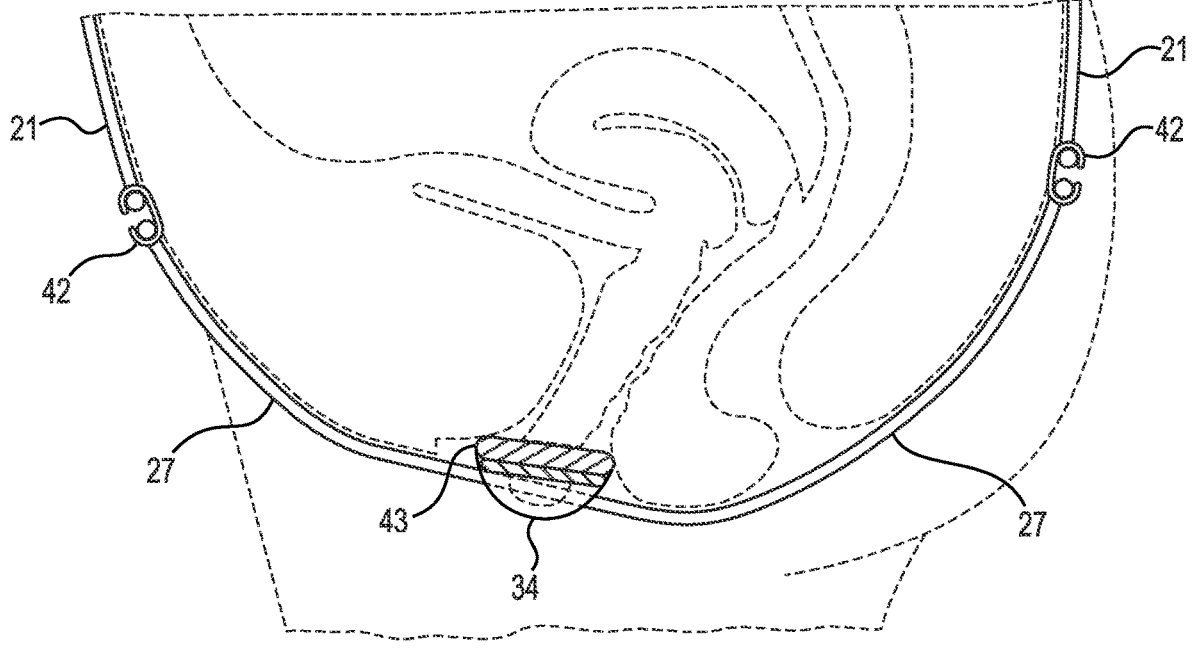
FIG. 4 is a cross sectional view of an embodiment of the leak control device worn by a user.

Use of the leakage control device 10 is particularly illustrated in FIGS. 3-7. To use the leakage control device 10, the user fastens or couples the one or more retraction mechanisms 16 to the front and rear parts or portions of an undergarment's waistband (see FIGS. 3 and 4). The user positions the end support members or straps 27 and bridge member 34 proximate the interior crotch portion of the users' undergarment. As the user pulls on the undergarment, the retracting members or cords 20 are pulled out of the housing 17 and presses the absorbent/sanitary article 43 and bridge member 34 of the slide assembly 31 against the urethral meatus. As a user continues to pull on the undergarment, the retracting member or cords 20 are continued to be pulled out of the housing 17 keeping pressure upon the absorbent/sanitary article 43 and bridge member 34. The user then places or adjusts the bridge member 34 by sliding it along the end support members 27. The absorbent/sanitary article 43 is ideally adjusted by positioning the bridge member 34 against the perineum opening(s), as shown in FIG. 4.

The retraction forces of the retraction mechanisms 16 tension the retracting members 20, intermediate support members 26, and end support members or straps 27 by generating a sufficient upward force on the bridge member 34 positioned on the end support members or cords 27. The predetermined and constant upward force presses the bridge member 34 against the perineum openings holding the bridge member 34 and/or absorbent/sanitary article 43 in close contact with the openings. Compression of the perineum prevents an involuntary leakage of bodily fluids and discharges when the pressure of a discharge is up to or below a predetermined pressure level, and alleviates and absorbs leakage of discharges, when their pressure is above the predetermined levels, via application of pressure resistance to and obstruction of liquid flow, thus controlling the flow from the openings. The predetermined pressure is not set too high to avoid the risk of vesicouretral reflux where urine goes back up to the kidneys resulting in reflux nephropathy over time.

The retracting member or cords' 20 retraction and upward compression forces remain constant and predetermined, keeping the bridge member 34 and/or absorbent/sanitary article 43 in close proximity with perineum openings regardless of the position of the undergarment's waistband with the attached retraction mechanisms 16 on the users' body and/or the users' panty styles. The article position and constant and predetermined pressure against the openings are not affected by vigorous motions of the user's body. One size of the device fits all users regardless of their body sizes, shapes, or the differences in anatomy of the perineum.

All the above factors may change pull-out length of the retracting member or cords 20 without a change in a value of the retraction mechanisms' 16 constant and predetermined retraction force. A disposable absorbable sanitary article 43 can be removably secured on the bridge member 34 by any means such as adhesive, snap fastener, hook and loop type attachment, etc. The leakage control device 10 can be used with a wide variety of readily available disposable or reusable absorbent sanitary articles, or with a custom shaped and designed pad, which is part of the invention concept. (The term disposable or reusable absorbent sanitary article 43 includes, but is not limited to, hygiene products such as incontinence pads, menstrual pads, liners, napkins, interlabial pads, and other sanitary products.)

Figures 5, 6, 7:
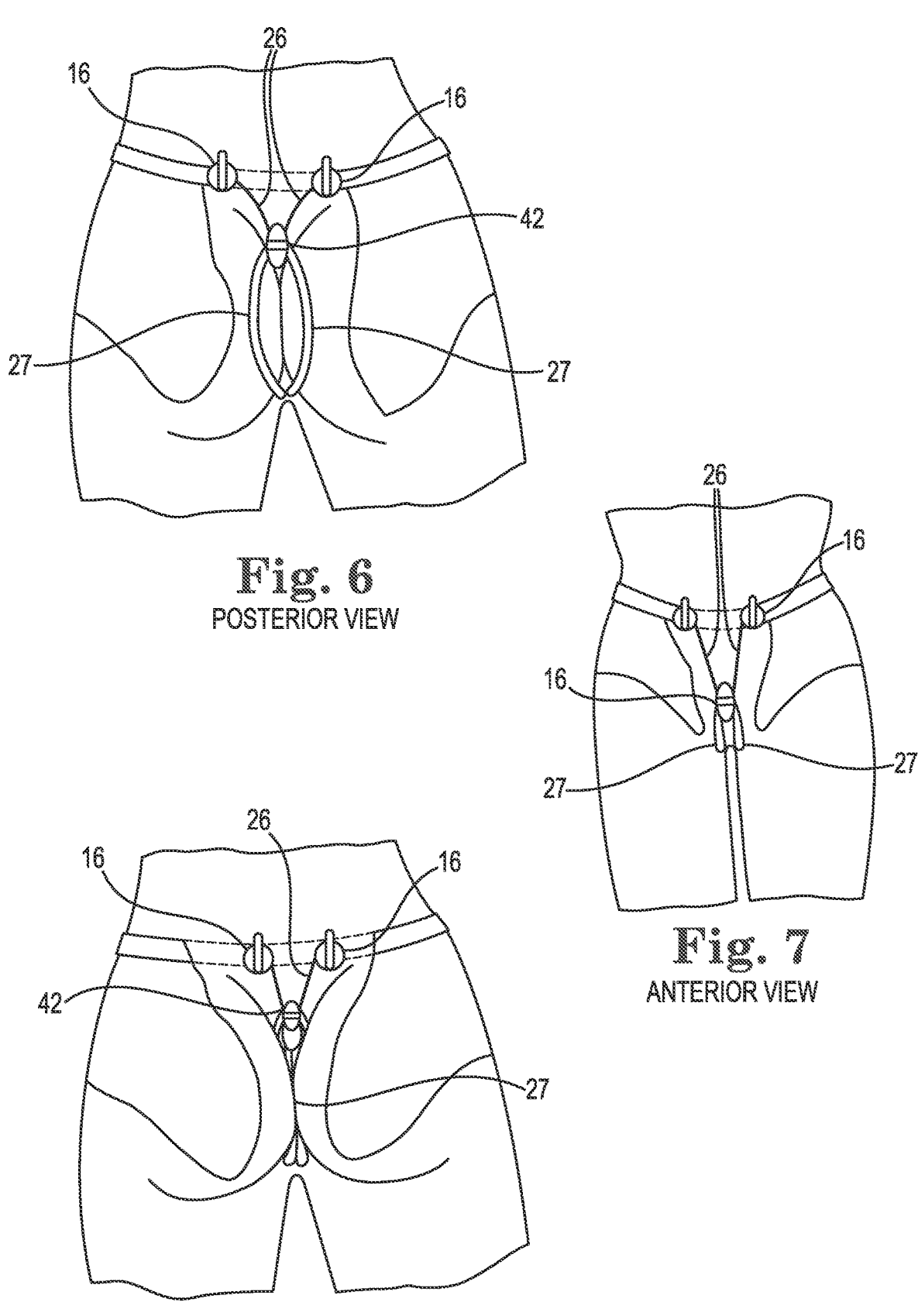
FIG. 5 is a rear view of an example embodiment of the leak control device as worn by user.
FIG. 6 is a rear view of an example embodiment of the leak control device as worn by a user.
FIG. 7 is a front view of an example embodiment of the leak control device as worn by a user.

Turning now to FIGS. 5-7, which are schematic illustrations of an example embodiment of the leakage control device 10, the retracting members or cords 20, intermediate support members 26 and end support members or straps 27 are shown in various positions on a user's body. As particularly shown in FIGS. 5 and 7, a portion of the support members or straps 27 may be positioned over the user's buttocks (see FIG. 6) or into the buttock's gluteal groove (see FIG. 5) depending on user's preference and/or on the type of user's panties or undergarment. FIGS. 14-20 illustrate another example embodiment of the present invention. In this particular example embodiment, retractor or retraction mechanisms 16 are coupled to a waistband of a users' undergarment, or to a belt member 60 that is secured about a waist of a user or user. The belt member 60 can comprise an elastic material, which allows it to stretch and contract to provide a universal fit for any user. The belt member 60 may also include a buckle or similar fastening mechanism to allow a user to adjust the belt member 60 around their waist. For the purpose of clarity, a belt member 60 is not necessary for the function and operation of the present invention. One skilled in the art will appreciate that the belt member 60 is optional and may be used with example embodiment of the present invention.

Similar to other embodiments, one or more end support members or straps 27, or combined intermediate support members 26 and end support members or straps 27 are operatively coupled to the retracting members or cords 20 of the retraction mechanisms 16 to provide consistent and constant and predetermined retracting force along their length. As particularly illustrated in FIGS. 14, 15, and 20, a bridge member 34 is extended between the end support members or straps 27. The bridge member 34 may have generally curved ends 62a and 62b that extend about a respective portion of the end support members or straps 27. An opening 64 between the curved ends 62a and 62b of the bridge member 34 enable easy adjustment or replacement of the bridge member 34. An absorbent/sanitary article 43 can be placed upon the bridge member 34 to capture any fluid that may accidently leak out of the orifice.

Referring to FIGS. 16-19, the housing 17 of the retraction mechanisms 16, have one or more covers 39 for selectively covering the interior cavity 22 of the housing 17. In this particular embodiment, two spaced apart posts 68a and 68b are positioned in the interior 17a (which is divided in at least a pair of interior sub-cavities 22a and 22b). The posts 68a and 68b are spaced apart and are able to each support a separate biasing member or spring 20 or assembly (not shown but similar to biasing member or spring 21 described above) comprising a spool 18, retracting member or cord 20, and a biasing member or spring 21.

The retracting member or cord 20 may extend through two openings 70a and 70b formed in the housing 17. In this configuration, each end support member or strap 27, or combination intermediate support member 26 and end support members or straps 27, are individually controlled by a separate retracting members or cords 20 and its respective consistent force. This enables an increase in the incremental adjustment of the leakage control device 10 to the movement of the user.

Turning now to the example embodiment illustrated in FIGS. 21 through 25, the bridge member or assembly 34 includes a front support portion 80a and a rear support portion 80b that each extend upwardly at an angle from the bridge member 34, whereby the bridge member 34 forms a generally saddle shape or configuration. The front support portion 80a is configured to provide a compressive force against a users' urethra while the rear support portion 80b is configured to provide a compressive force against a users' anus. While the bridge member 34 is illustrated as having both a front support portion 80a and a rear support portion 80b, one skilled in the art will appreciate that the bridge member or assembly 34 may have only a front support portion 80a or a rear support portion 80b, depending upon the condition and needs of the user.

As particularly illustrated in FIG. 21, the front support portion 80a and/or rear support portion 80b may have a bifurcation 82 formed in them creating branches 83 that extend laterally along opposed sides of the orifice being treated. The front support portion 80a and rear support portion 80b may have any number of bifurcations and branches 83, with the individual branches 83 having any shape or configuration. Additionally, the bridge member 34 may be manufactured branches 34 that are generally flexible to move and press against the user.

The branches 83 and their flexibility also help to protect a user's skin from the retracting members or cords 20 or the end support members or straps 27 while also providing overall comfort to the user. As illustrated in FIGS. 29A, 29B, 30A, 31A, and 31B, the branches 34 are positioned between the user's skin and retracting members or cords 20, or the end support members or straps 27. A lower surface of the branches 34 may also comprise one or more guides (not shown) that retain the retracting members or cords 20, or the end support members or straps 27 over each of the branches 34. The guides are configured to allow free movement of the retracting members or cords 20, or the end support members or straps 27 through them so as to not interfere with the operation of the leakage control device 10.

Figure 24:
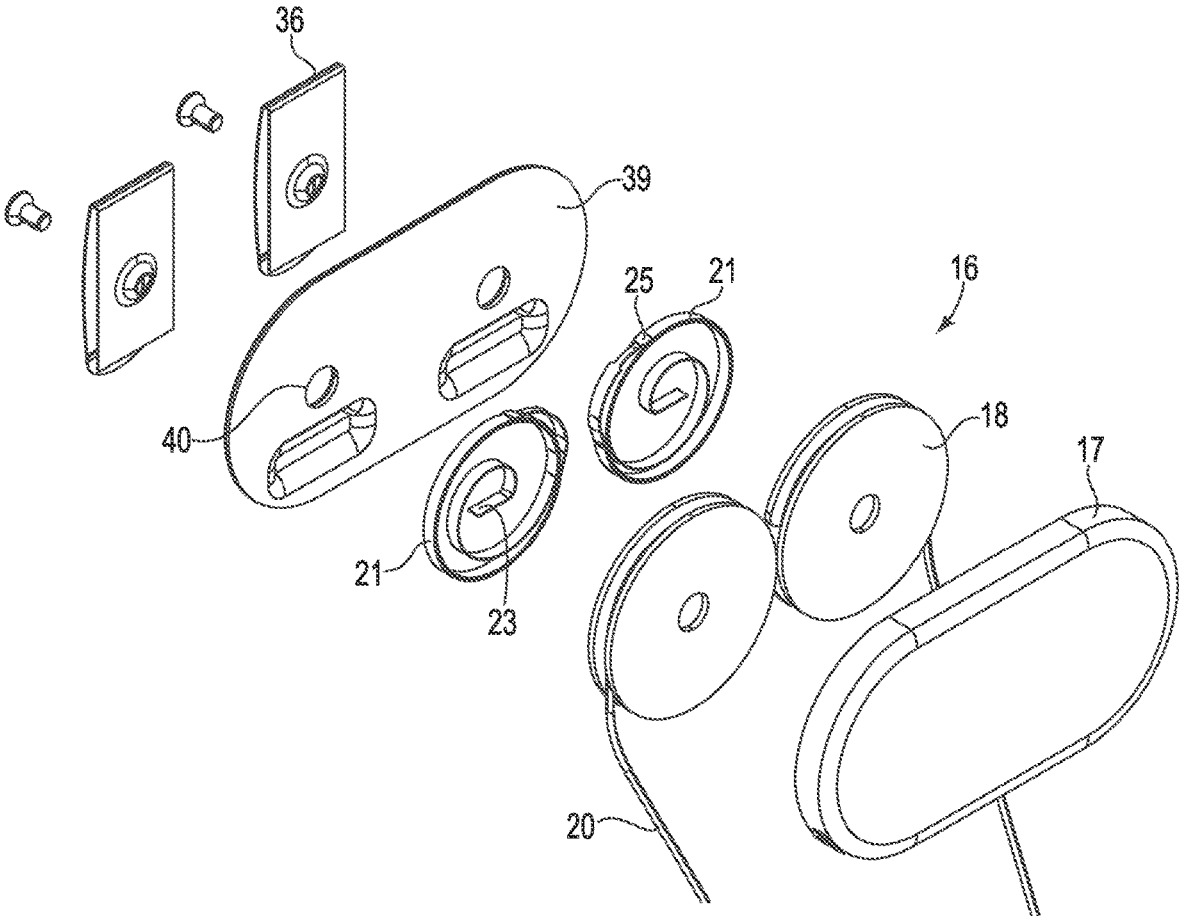
FIGS. 24 and 25 are exploded views of the example retraction mechanisms of FIGS. 22 and 23 respectively.

FIGS. 23 and 24 illustrate the front and back surfaces, respectively, of the retractors or retraction mechanisms 16. As particularly illustrated in FIG. 23, there can be more than one fastening member 36 formed on or attached to the housing 17. As discussed above, the fastening member 36 can comprise a clip that fits over a user's garment or an optional waistband. In another example embodiment, the housing 17 can comprise one or more openings or slits/slots that are configured to receive an optional belt member 60.

The belt member 60 can be passed or threaded through the slits or slots and then secured about the waist of the user.

Figure 25:
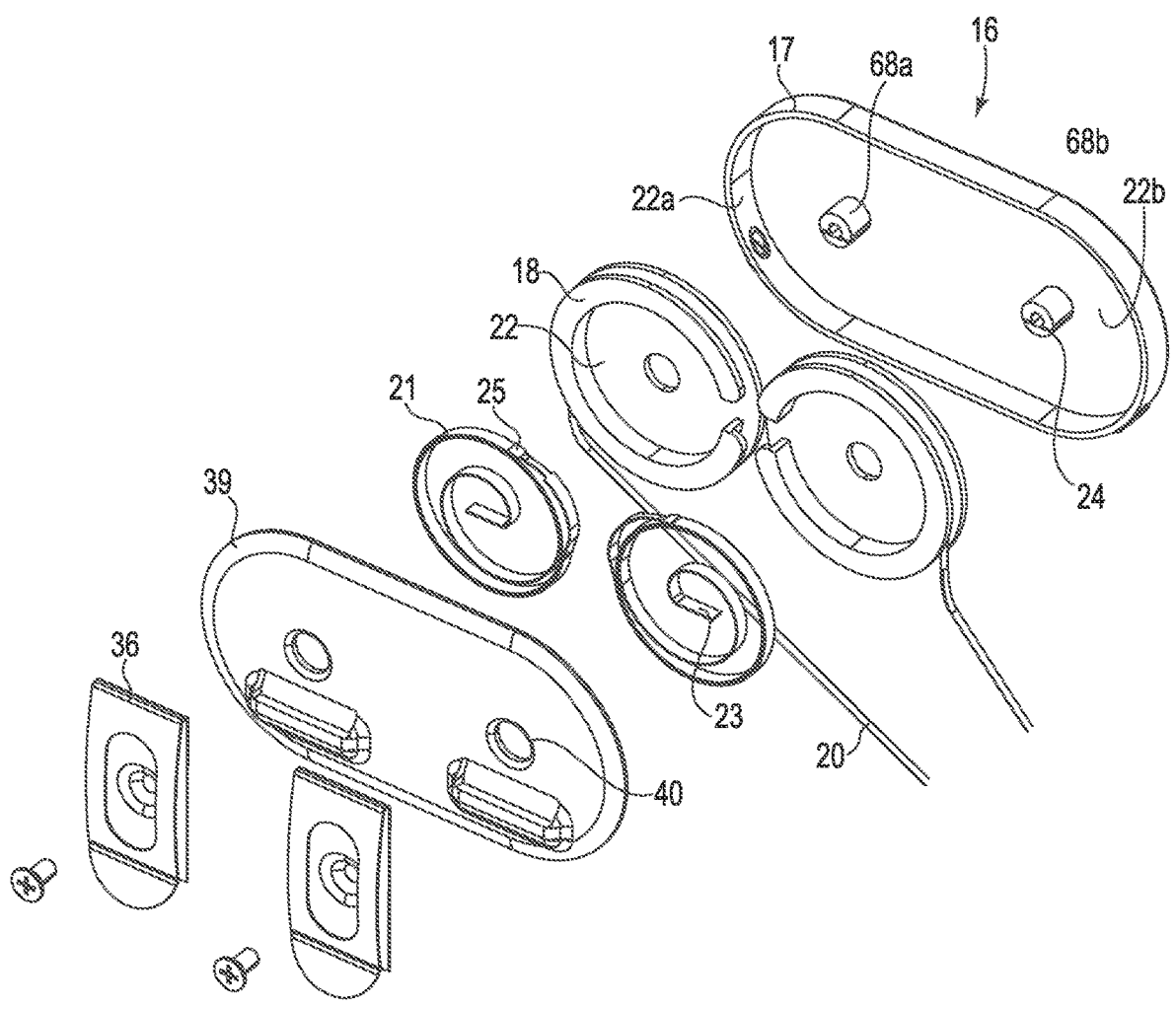

Turning to FIGS. 24 and 25, a retractor or retraction mechanism 16 is illustrated in an exploded view to show an example assembly of the biasing members or springs 21 and spools 18 within the housing 17. FIGS. 26 through 28 show the biasing members or springs 21 coupled to the spools 18 and coupled to the posts 68*a* and 68*b* of the housing 17. As particularly illustrated in FIGS. 27 and 28, an outer end 25 of the biasing members or springs 21 comprise a configuration (e.g., such as opposed notches) formed therein that are designed to secure the biasing members or springs 21 to a portion of the spool 18.

Figure 29A:
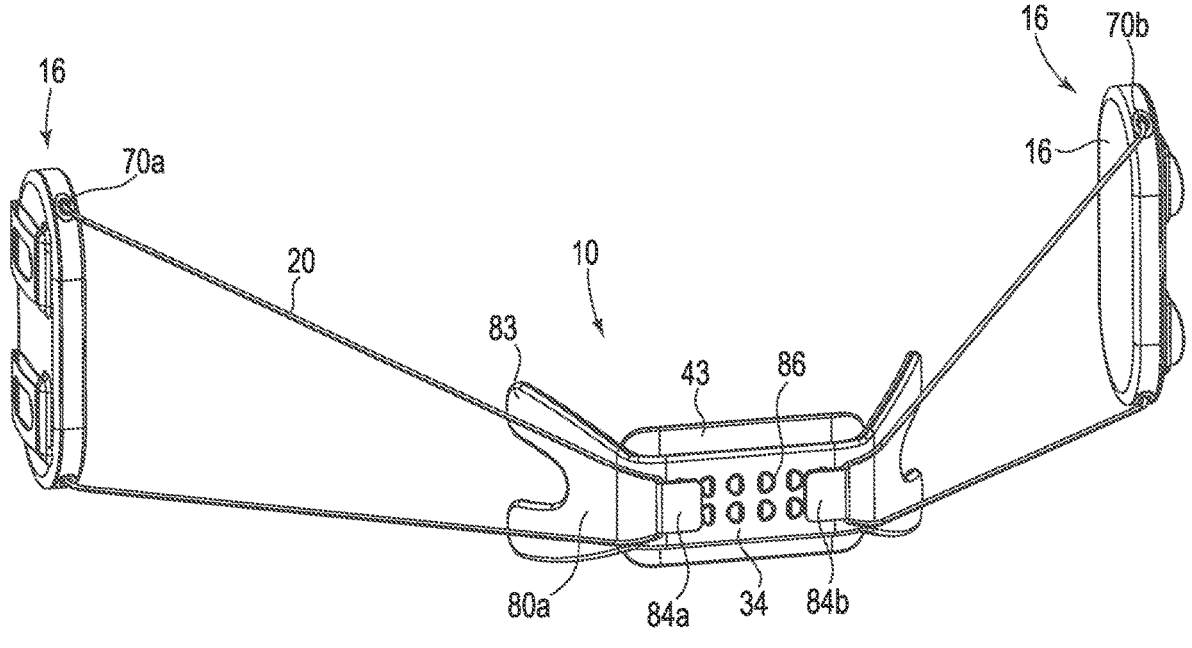
FIG. 29A is a perspective view of an example embodiment of the leak control device showing bottom connectors.
Figure 29B:
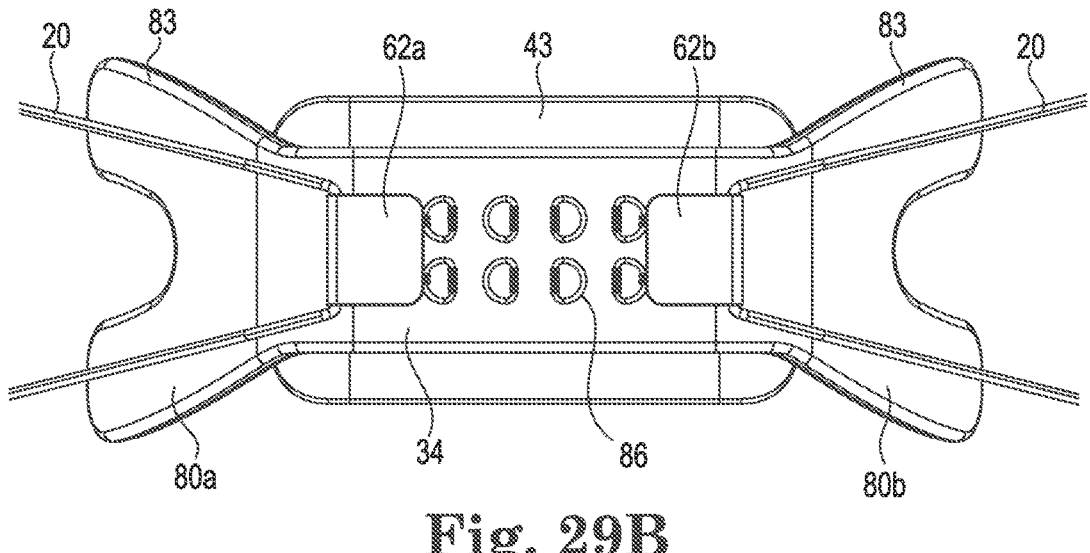
FIG. 29B is a bottom view of an example embodiment of the leak control device showing bottom connectors.

In this particular embodiment of the present invention, the leak control device 10 includes additional adjustments that can be made at the bridge member 34. As illustrated in FIGS. 29A, and 29B, each of the retracting members or cords 20 includes an attachment or hook member 84*a* and 84*b*, respectively. The hook members 84*a* and 84*b* can comprise a generally planar coupling portion having an opening or channel for receiving the retracting members or cords 20 proximate the bridge member 34. The hook members 84*a* and 84*b* also comprise one or more hook portions extending from the coupling portion that are configured to engage or mate with one or more loop or eye members 86 disposed on a bottom of the bridge member 34.

Figure 30A:
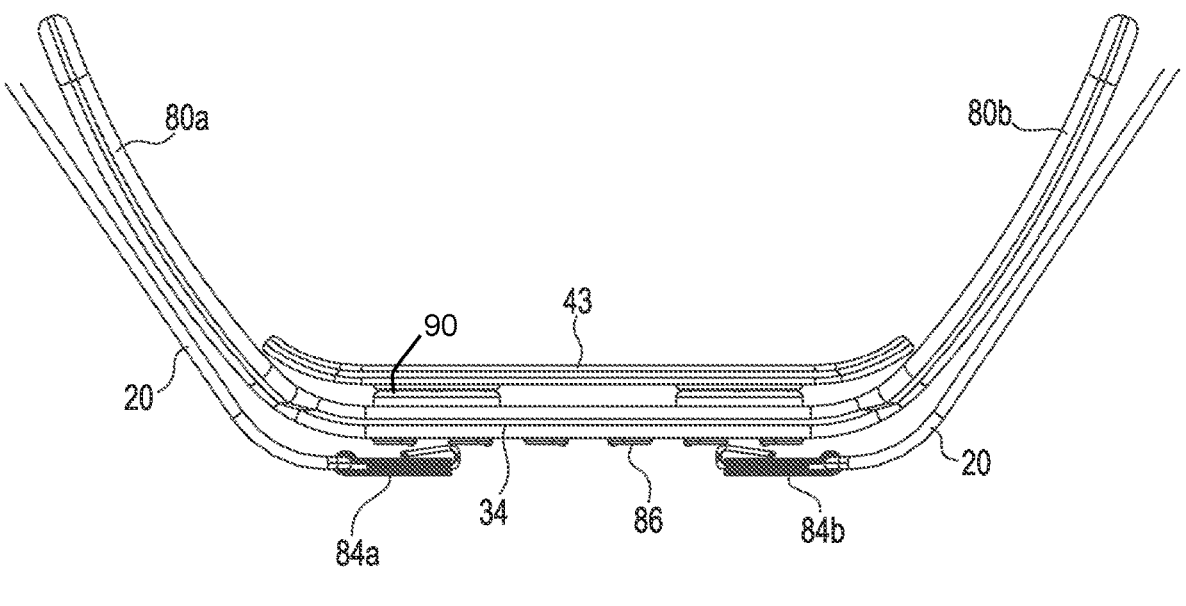
FIG. 30A is a side view of an example embodiment of the leak control device in an assembled configuration.
Figure 30B:
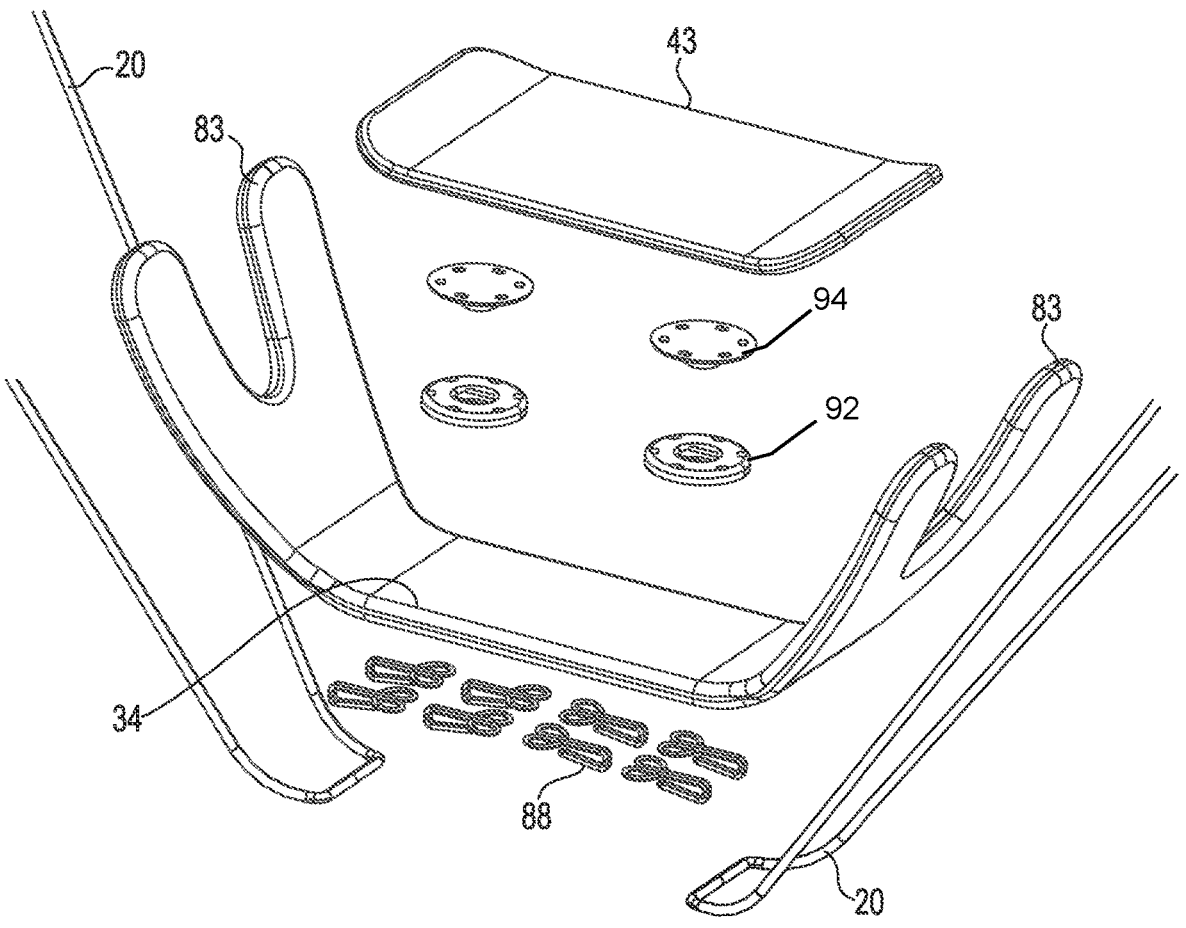
FIG. 30B is an exploded view of an example embodiment of the leak control device.
Figure 31A:
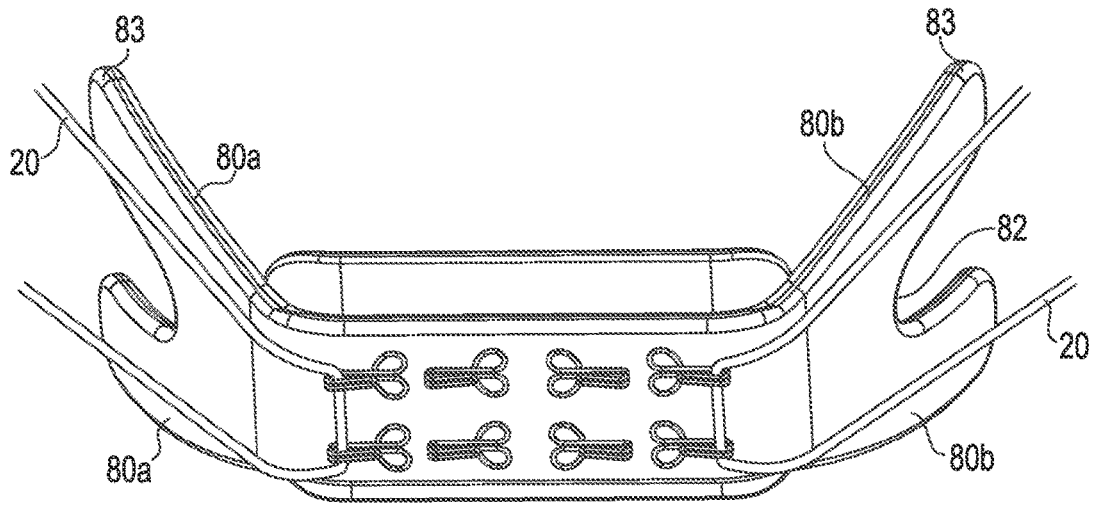
FIG. 31A is a perspective view of an example embodiment of the leak control device showing bottom connectors.

In another example embodiment of the invention, as illustrated in FIGS. 30B and 31A, one or more hook members 88 are attached to the bottom of the bridge member 34. In this configuration, ends of each of the retracting members or cords 20 are able to be hooked onto or over the hook members 88. The loop or eye members 86 or hook members 88 can be arranged in successive rows to allow a user to adjust the attachment point of the retracting members or cords 20 to the bridge member 34.

Figure 31B:
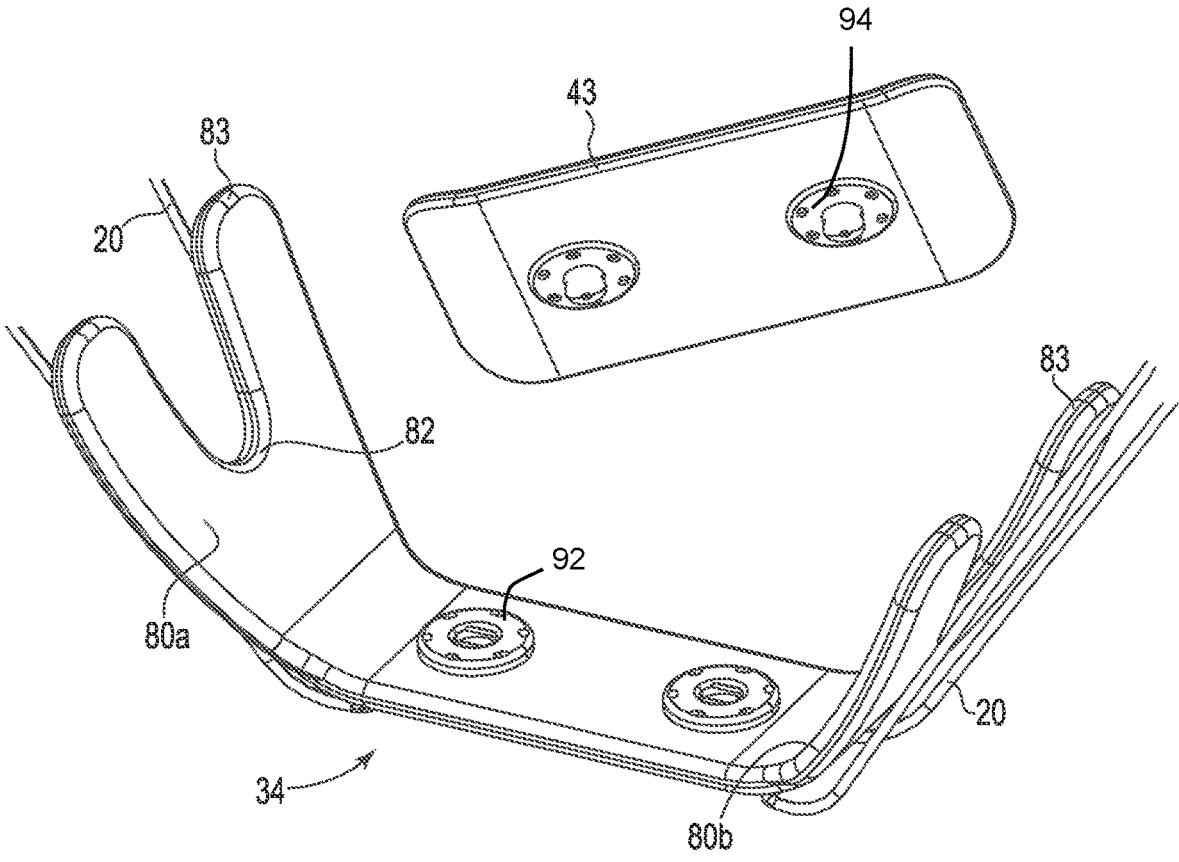
FIG. 31B is an exploded view of an example embodiment of the leak control device showing top surface receptacles and an absorbent member having bottom surface connectors or posts that can mate with the receptacles.

In order to prevent movement of the absorbent member 43, the leakage control device comprise one or more securing mechanism 90 secured to and extending between the bridge member 34 and the absorbent member 43. As illustrated in FIGS. 30A, 30B, and 31B, the securing mechanism can comprise a snap fastener having a socket portion 92 configured to receive a post or post and ball portion 94. The figures of the present invention illustrate the socket portion 92 disposed on the bridge member 34 and the post portion 94 disposed on the absorbent member 43. However, one skilled in the art will appreciate that the socket portion 92 may be disposed on the absorbent member 43 and the post portion 94 may be disposed on the bridge member 34. Additionally, other types of securing mechanisms can also be used and should be considered to be within the spirit and scope of the invention.

The leak control device 10 may be made with a retraction mechanism (e.g. clock spring or power spring) or type of constant force mechanism other than the mechanism described herein, although mechanisms with more complex designs would likely be more costly to produce and complex to use. Regardless, the mechanisms' way of function should not affect the functional advantages of the devices of the present invention. Although examples of particular embodiments of the present invention have been illustrated and described below, various other changes and modifications can be made without departing from the spirit and scope of the invention. It is therefore intended to cover all such changes and modifications that are within the scope of the invention.

What is claimed is:

1. A perineum control device for applying pressure to the perineum region of a user, the perineum control device being attachable to a portion of an undergarment or belt and having a perineum covering region or portion, the perineum control device comprising:
   a rotatable spool being attachable to a portion of the undergarment or the belt;
   a cord member in operative communication with the retractor rotatable spool and positionable against the user's perineum, wherein operation of the rotatable spool exerts a force on the cord member;
   a band member coupled to a portion of the cord member and is configured to be positionable against the user's perineum, wherein the band is movable with respect to the cord member; and
   wherein the rotatable spool is configured to retract the cord member causing a constant upward force on the cord member, which causes a constant and predetermined force being applied to the band member, which is configured to apply the force against the perineum region of the user.

2. The perineum control device of claim 1, wherein the rotatable spool comprises a first rotatable spool and a second rotatable spool, each being in operative communication with the cord member.

3. The perineum control device of claim 2, wherein the rotatable spool comprises a first rotatable spool and second rotatable spool and the cord member comprises
   a first cord member being at least partially spooled on the first rotatable spool and a second cord member being at least partially spooled on the second rotatable spool and
   a first spring member and a second spring member, each spring member being configured to move the first rotatable spool and the first cord member and the second rotatable spool and second cord member, respectively from an extended state to a retracted state such that the first spring member and second spring member each applies the constant and predetermined upward force on the first cord member and the second cord member.

4. The perineum control device of claim 1, wherein the band member comprises:
   a front support portion configured to support a front of the perineum region of a user;
   a rear support portion configured to support a rear of the perineum region of a user; and
   wherein the front support portion and rear support portion each extend at an angle away from the band member.

5. The perineum control device of claim 4, further comprising:
   a pad member disposed on an upper surface of the band member and positionable against the perineum, the pad member having a shape approximating a shape of the band member;
   a fastener disposed on the upper surface of the band member and configured to fasten the pad member to the band member; and wherein the pad member is configured to absorb a fluid.

6. The perineum control device of claim 1, further comprising:
   a pad member disposed on an upper surface of the band member and is configured to be positionable against the perineum;
   a fastener disposed on the upper surface of the band member and configured to fasten the pad member to the band member; and
   wherein the pad member is configured to absorb a fluid.

7. The perineum control device of claim 6, further comprising:

a first cord member extending between and being retractably coupled to the rotatable spool configured to be positioned on a back of a user;

a second cord member extending between and being retractably coupled to the second pair of rotatable spools;

an end support member extending between the first cord member and the second cord member, the band member being supported by a portion of the end support member;

connectors being coupled to and extending between portions of the first cord member and the second cord member; and wherein the end support member is configured to extend across the perineum region of a user.

8. The perineum control device of claim 1, further comprising an end support member coupled to the cord member and the band member.

9. The perineum control device of claim 1, wherein the rotatable spool further comprising:

a housing for retaining the rotatable spool, wherein the cord member is at least partially spooled on the rotatable spool;

a spring member in operative communication with the rotatable spool; and wherein the spring member is configured to move the rotatable spool and cord from an extended state to a retracted state such that the spring member applies the constant upward force on the cord member.

10. The perineum control device of claim 1, further comprising:

a connector disposed on a portion of the band member and configured to adjustably couple a portion of the cord to the band member.

11. The perineum control device of claim 1, wherein the rotatable spool comprises a pair of first rotatable spools and a pair of second rotatable spools, the first pair of rotatable spools and the second pair of rotatable spools each being in operative communication.

12. The perineum control device of claim 1, further comprising a stopper coupled to a portion of the cord member and selectively abuttable against an opening in the rotatable spool, wherein the stopper is configured to stop the cord member at a predetermined retraction point.

13. A method for applying pressure to a perineum region of a user, the user wearing a garment having a belt member, the method comprising the steps of:

providing a front spool member configured to couple to a front portion of the belt member, the front spool member having a front cord member;

providing a rear spool member configured to couple to a rear portion of the belt member, the rear spool member having a rear cord member;

providing a band member configured to be coupled to and extend between the front cord member and the rear cord member, wherein the band member is configured to be positioned against the perineum region of the user; and wherein the front spool member and rear spool member are configured to apply a constant and predetermined pulling force onto the front cord member and the rear cord member that causes the band member to press against the perineum region.

14. The method for applying pressure to a perineum region of claim 13, further comprising the steps of providing a connector coupled to a portion of the band member, the connector being configured to adjustably couple the band member to the front cord member and the rear cord member.

15. The method for applying pressure to a perineum region of claim 14, wherein the connector comprises one or more hook members coupled to a portion of the band member, wherein the one or more hook members are configured to receive a portion of the front cord member and a portion of the rear cord member.

16. The method for applying pressure to a perineum region of claim 15, wherein the one or more hook members comprises a first set of hook members configured in a first orientation to receive the front cord member and a second set of hook members configured to a second orientation to receive the rear cord member, wherein first set of hook members and second set of hook members are oriented opposite of each other.

17. The method for applying pressure to a perineum region of claim 14, wherein the connector comprises a clip.

18. The method for applying pressure to a perineum region of claim 13, wherein the step of providing a front spool member comprises providing a pair of front spool member and the step providing a rear spool member comprises providing a pair of rear spool member.

19. The method for applying pressure to a perineum region of claim 13, further comprising the step of providing a pad member disposed on a portion of the band member, wherein the pad member is configured to absorb any body fluids.

20. The method for applying pressure to a perineum region of claim 13, further comprising the step of providing a pad member removably disposed on a portion of the band member, wherein the band member and pad member are provided in a saddle configuration configured to be conformable to the perineum region of the user.

\*  \*  \*  \*  \*